(12) United States Patent
Curtis et al.

(10) Patent No.: US 7,125,687 B1
(45) Date of Patent: Oct. 24, 2006

(54) PRESENILIN ENHANCERS ASSAYS

(75) Inventors: Daniel Tim Curtis, South San Francisco, CA (US); George Ross Francis, South San Francisco, CA (US); Michael Christopher Ellis, South San Francisco, CA (US); David Andrew Ruddy, South San Francisco, CA (US); Sharmon Monique Nicoll, South San Francisco, CA (US); Garth Joseph McGrath, South San Francisco, CA (US)

(73) Assignee: Exelixis, Inc., So. San Francisco, CA (US)

( * ) Notice: Subject to any disclaimer, the term of this patent is extended or adjusted under 35 U.S.C. 154(b) by 611 days.

(21) Appl. No.: 09/568,942

(22) Filed: May 5, 2000

(51) Int. Cl.
*C12P 21/06* (2006.01)
*C12N 5/00* (2006.01)
*C12N 15/00* (2006.01)
*A01N 43/04* (2006.01)
*A61K 31/715* (2006.01)

(52) U.S. Cl. ............... 435/69.1; 435/325; 435/455; 800/21; 514/44

(58) Field of Classification Search ............... 435/4, 435/6, 7.1, 7.2, 7.21, 7.32, 7.4
See application file for complete search history.

(56) References Cited

U.S. PATENT DOCUMENTS 6,278,039 B1 * 8/2001 Johnson et al. ............... 800/8

FOREIGN PATENT DOCUMENTS

| WO | 98/21328 | 5/1998 |
|---|---|---|
| WO | WO 98/21328 | 5/1998 |
| WO | WO 98/55508 | 12/1998 |
| WO | 99/06548 | 2/1999 |
| WO | 99/31236 | 6/1999 |
| WO | WO 00/00610 | 1/2000 |
| WO | WO 00/60069 | 10/2000 |

OTHER PUBLICATIONS

Smye et al., Science 282:2012-2018, 1998.*
Genbank Accession No. HS0078, T26007 Oct. 15,1 999.*
Link et al., PNAS 92:9368-72, Sep. 1995.*
Baumeister et al., Genes and Function, 1(2):149-159, 1997.*
Skolnick et al., Trends in Biotech., 18(1):34-39, 2000.*
Jobling et al, Mol. Microbiol., 1991, 5(7):1755-67.*
Tabara et al., Science, 282:430-431.*
Crooke et al., Antisense & Nucleic Acid Drug Dev., 8:115-122, 1998.*
Genbank Accession No. CEVF36H2L, AL021466 Jan. 23, 1998.*
Wilkinson, J., Direct Submission to GenBank, Accession No. CAB00063, Jul. 9, 1996.
Goutte, "aph-2 encodes a novel extracellular protein required for GLP-1-mediated signaling", published on WWW May 10, 2000; Development 127, pp. 2481-2492.

* cited by examiner

*Primary Examiner*—Sharon Turner
(74) *Attorney, Agent, or Firm*—Richard Aron Osman

(57) ABSTRACT

The invention provides methods and compositions relating to pen polypeptides having pen-specific structure and activity, related polynucleotides and modulators of pen function. The invention provides isolated pen hybridization probes and primers capable of specifically hybridizing with natural pen genes, pen-specific binding agents such as specific antibodies, and methods of making and using the subject compositions in diagnosis (e.g. genetic hybridization screens for pen transcripts), therapy (e.g. pen inhibitors to modulate APP processing) and in the biopharmaceutical industry (e.g. as immunogens, reagents for screening chemical libraries for lead pharmacological agents, etc.).

28 Claims, No Drawings

SEQUENCE LISTING

```
<160> NUMBER OF SEQ ID NOS: 38

<210> SEQ ID NO 1
<211> LENGTH: 308
<212> TYPE: PRT
<213> ORGANISM: Caenorhabditis elegans

<400> SEQUENCE: 1

Met Gly Tyr Leu Leu Thr Ile Ala Cys Tyr Ile Ala Ser Phe Ser Pro
 1               5                  10                  15

Ser Ile Ala Leu Phe Cys Ser Phe Ile Ala His Asp Pro Val Arg Ile
            20                  25                  30

Ile Leu Phe Phe Leu Gly Ser Phe Phe Trp Leu Val Ser Leu Leu Phe
        35                  40                  45

Ser Ser Leu Ala Trp Leu Gly Leu Ser Thr Val Leu Pro Asp Thr Phe
    50                  55                  60

Leu Leu Ser Leu Thr Val Cys Ile Ile Ala Gln Glu Leu Ser Arg Val
65                  70                  75                  80

Ala Tyr Phe Met Leu Leu Lys Lys Ala Gln Arg Gly Leu Asn Lys Ile
                85                  90                  95

Thr Arg Gln Gly Gln Ile Ser Val Ala Pro Gly Val Ser Asp Leu His
            100                 105                 110

Asn Ala Arg His Met Leu Ala Leu Val Cys Gly Leu Gly Met Gly Val
```

```
            115                 120                 125
Ile Ser Ala Leu Phe Tyr Thr Met Asn Ala Phe Ala Ile Phe Ser Gly
        130                 135                 140

Pro Gly Thr Ile Gly Leu Pro Asn Ala Leu Lys Thr Gly Glu Ile Asp
145                 150                 155                 160

Thr Asn Arg Ala Gly Lys Tyr Leu Pro Leu Cys Tyr Thr Leu Ser Ala
                165                 170                 175

Ile Leu Leu Thr Leu Phe His Val Thr Trp Thr Ile Met Val Trp Asp
                180                 185                 190

Ser Cys His Lys Ile Gly Arg Ile Pro Ser Ala Phe Val Pro Gly Ala
                195                 200                 205

Ala Ala Val Val Ser His Leu Leu Val Thr Phe Leu Ser Ser Leu Asn
        210                 215                 220

Ser Arg Gly Phe His Val Leu Val Phe Ala Val Gln Phe Leu Ile Leu
225                 230                 235                 240

Leu Ile Cys Ile Ala Tyr Cys Asn Val Ile Met Gly Gly Thr Ile Ser
                245                 250                 255

Ser Phe Val Asn Gly Ile Gly Gln Ser Ile Thr Asp Ala Val Thr Leu
                260                 265                 270

Lys Gln Val Arg Thr Leu Ile Glu Glu Arg Lys Leu Arg Thr Gln Arg
                275                 280                 285

Gln Ser Val Pro Asp Glu Pro Met Thr Glu Arg Ala Gly Thr Ser Asn
        290                 295                 300

Thr Val Asn Ala
305

<210> SEQ ID NO 2
<211> LENGTH: 238
<212> TYPE: PRT
<213> ORGANISM: Drosophila melanogaster

<400> SEQUENCE: 2

Met Thr Leu Pro Glu Phe Phe Gly Cys Thr Phe Ile Ala Phe Gly Pro
  1               5                  10                  15

Pro Phe Ala Leu Phe Val Phe Thr Ile Ala Asn Asp Pro Val Arg Ile
                 20                  25                  30

Ile Ile Leu Ile Ala Ala Ala Phe Phe Trp Leu Leu Ser Leu Leu Ile
             35                  40                  45

Ser Ser Leu Trp Tyr Ala Leu Ile Pro Leu Lys Glu Phe Leu Ala Phe
         50                  55                  60

Gly Val Val Phe Ser Val Cys Phe Gln Glu Ala Phe Arg Tyr Ile Ile
 65                  70                  75                  80

Tyr Arg Ile Leu Arg Ser Thr Glu Gln Gly Leu His Ala Val Ala Glu
                 85                  90                  95

Asp Thr Arg Val Thr Asp Asn Lys His Ile Leu Ala Tyr Val Ser Gly
            100                 105                 110

Leu Gly Phe Gly Ile Ile Ser Gly Met Phe Ala Leu Val Asn Val Leu
        115                 120                 125

Ala Asp Met Ser Gly Pro Gly Thr Met Gly Leu Lys Gly Gly Thr Glu
        130                 135                 140

Leu Phe Phe Val Thr Ser Ala Ala Gln Ala Leu Ser Ile Ile Leu Leu
145                 150                 155                 160

His Thr Phe Trp Ser Val Ile Phe Phe Asn Ala Phe Asp Thr Asn Asn
                165                 170                 175
```

-continued

Tyr Ile His Ile Gly Tyr Val Val Phe Ser His Leu Phe Val Ser Leu
            180                 185                 190

Ile Thr Leu Leu Asn Ala Asn Glu Leu Tyr Thr Thr Thr Leu Leu Ile
        195                 200                 205

Asn Tyr Leu Val Thr Ile Leu Thr Gly Val Leu Ala Phe Arg Val Ala
    210                 215                 220

Gly Gly Thr Ser Arg Ser Phe Arg Lys Phe Ile Thr Cys Gln
225                 230                 235

<210> SEQ ID NO 3
<211> LENGTH: 126
<212> TYPE: PRT
<213> ORGANISM: Heliothis virescens

<400> SEQUENCE: 3

Met Thr Leu Ala Glu Phe Phe Ser Cys Ser Leu Leu Ala Phe Gly Ala
1               5                   10                  15

Pro Leu Val Met Phe Ala Leu Thr Val Ala Asn Asp Pro Val Arg Ile
            20                  25                  30

Ile Ile Met Ile Ala Ala Ala Phe Gly Trp Leu Leu Ser Phe Leu Val
        35                  40                  45

Ser Ser Val Val Trp Tyr Ala Val Val Pro Leu Arg Ser Tyr Leu Ala
    50                  55                  60

Phe Gly Met Val Phe Ala Ile Ile Phe Gln Glu Val Phe Arg Tyr Gly
65                  70                  75                  80

Met Tyr Val Leu Leu Arg Lys Thr Glu Ala Gly Leu Lys Glu Ile Ser
                85                  90                  95

Glu Asn His Asn Ile Gly Ser Asn Lys Leu Glu Met Ala Tyr Val Ser
            100                 105                 110

Gly Leu Gly Phe Gly Thr Met Ser Gly Ala Phe Ala Leu Ile
        115                 120                 125

<210> SEQ ID NO 4
<211> LENGTH: 244
<212> TYPE: PRT
<213> ORGANISM: mouse

<400> SEQUENCE: 4

Met Gly Ala Ala Val Phe Phe Gly Cys Thr Phe Val Ala Phe Gly Pro
1               5                   10                  15

Ala Phe Ser Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
    130                 135                 140

```
Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
        210                 215                 220

Gly Leu Trp Ala Phe Ile Thr Ala Gly Val Pro Ser Glu Val Ser Ser
225                 230                 235                 240

Ala Ala Phe Val

<210> SEQ ID NO 5
<211> LENGTH: 251
<212> TYPE: PRT
<213> ORGANISM: human

<400> SEQUENCE: 5

Met Gly Ala Ala Val Phe Phe Gly Cys Thr Phe Val Ala Phe Gly Pro
  1               5                  10                  15

Ala Phe Ala Leu Phe Leu Ile Thr Val Ala Gly Asp Pro Leu Arg Val
                 20                  25                  30

Ile Ile Leu Val Ala Gly Ala Phe Phe Trp Leu Val Ser Leu Leu Leu
             35                  40                  45

Ala Ser Val Val Trp Phe Ile Leu Val His Val Thr Asp Arg Ser Asp
         50                  55                  60

Ala Arg Leu Gln Tyr Gly Leu Leu Ile Phe Gly Ala Ala Val Ser Val
 65                  70                  75                  80

Leu Leu Gln Glu Val Phe Arg Phe Ala Tyr Tyr Lys Leu Leu Lys Lys
                 85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
        210                 215                 220

Gly Leu Trp Ala Phe Ile Thr Ala Gly Gly Ser Leu Arg Ser Ile Gln
225                 230                 235                 240

Arg Ser Ser Cys Val Arg Thr Asp Tyr Leu Asp
                245                 250

<210> SEQ ID NO 6
<211> LENGTH: 257
```

```
<212> TYPE: PRT
<213> ORGANISM: human

<400> SEQUENCE: 6

Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Phe Trp Leu Val Ser Leu Leu Ile
        35                  40                  45

Ser Ser Leu Val Trp Phe Met Ala Arg Val Ile Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Gln Glu Met Phe Arg Phe Ala Tyr Tyr Lys Leu Leu Lys Lys
                85                  90                  95

Ala Ser Glu Gly Leu Lys Ser Ile Asn Pro Gly Glu Thr Ala Pro Ser
            100                 105                 110

Met Arg Leu Leu Ala Tyr Val Ser Gly Leu Gly Phe Gly Ile Met Ser
        115                 120                 125

Gly Val Phe Ser Phe Val Asn Thr Leu Ser Asp Ser Leu Gly Pro Gly
130                 135                 140

Thr Val Gly Ile His Gly Asp Ser Pro Gln Phe Leu Tyr Ser Ala
145                 150                 155                 160

Phe Met Thr Leu Val Ile Ile Leu Leu His Val Phe Trp Gly Ile Val
                165                 170                 175

Phe Phe Asp Gly Cys Glu Lys Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205

Tyr Gly Ile Asn Leu Ala Ser Ala Phe Ile Ile Leu Val Leu Met Gly
    210                 215                 220

Thr Trp Ala Phe Leu Ala Ala Gly Gly Ser Cys Arg Ser Leu Lys Leu
225                 230                 235                 240

Cys Leu Leu Cys Gln Asp Lys Asn Phe Leu Leu Tyr Asn Gln Arg Ser
                245                 250                 255

Arg

<210> SEQ ID NO 7
<211> LENGTH: 101
<212> TYPE: PRT
<213> ORGANISM: Caenorhabditis elegans

<400> SEQUENCE: 7

Met Asp Ile Ser Lys Leu Thr Asp Val Lys Val Asp Leu Cys Lys
1               5                   10                  15

Lys Tyr Phe Leu Ile Gly Ala Cys Phe Leu Pro Leu Val Trp Ile Val
            20                  25                  30

Asn Thr Phe Trp Phe Phe Ser Asp Ala Phe Cys Lys Pro Ile Asn Ala
        35                  40                  45

His Arg Arg Gln Ile Arg Lys Tyr Val Ile Ala Ser Ile Val Gly Ser
    50                  55                  60

Ile Phe Trp Ile Ile Val Leu Ser Ala Trp Glu Ile Phe Gln His
65                  70                  75                  80

Tyr Arg Ala Gln Gly Leu Val Trp Thr Asp Phe Leu Thr Phe Val Phe
```

```
                        85                  90                  95

Pro Thr Gly Arg Val
            100

<210> SEQ ID NO 8
<211> LENGTH: 101
<212> TYPE: PRT
<213> ORGANISM: Drosophila melanogaster

<400> SEQUENCE: 8

Met Asn Ile Ser Lys Ala Pro Asn Pro Arg Lys Leu Glu Leu Cys Arg
 1               5                  10                  15

Lys Tyr Phe Phe Ala Gly Phe Ala Phe Leu Pro Phe Val Trp Ala Ile
            20                  25                  30

Asn Val Cys Trp Phe Phe Thr Glu Ala Phe His Lys Pro Pro Phe Ser
        35                  40                  45

Glu His Ser Gln Ile Lys Arg Tyr Val Ile Tyr Ser Ala Val Gly Thr
    50                  55                  60

Leu Phe Trp Leu Ile Val Leu Thr Ala Trp Ile Ile Ile Phe Gln Thr
65                  70                  75                  80

Asn Arg Thr Ala Trp Gly Ala Thr Ala Asp Tyr Met Ser Phe Ile Ile
                85                  90                  95

Pro Leu Gly Ser Ala
            100

<210> SEQ ID NO 9
<211> LENGTH: 101
<212> TYPE: PRT
<213> ORGANISM: rat

<400> SEQUENCE: 9

Met Asn Leu Glu Arg Val Ser Asn Glu Glu Lys Leu Asn Leu Cys Arg
 1               5                  10                  15

Lys Tyr Tyr Leu Gly Gly Phe Ala Phe Leu Pro Phe Leu Trp Leu Val
            20                  25                  30

Asn Ile Phe Trp Phe Phe Lys Glu Ala Phe Phe Ala Pro Ala Tyr Ser
        35                  40                  45

Glu Gln Ser Gln Ile Lys Gly Tyr Val Trp Arg Ser Ala Val Gly Phe
    50                  55                  60

Leu Phe Trp Val Ile Val Leu Thr Thr Trp Ile Thr Ile Phe Gln Ile
65                  70                  75                  80

Tyr Arg Pro Arg Trp Gly Ala Leu Gly Asp Tyr Leu Ser Phe Thr Ile
                85                  90                  95

Pro Leu Gly Thr Pro
            100

<210> SEQ ID NO 10
<211> LENGTH: 101
<212> TYPE: PRT
<213> ORGANISM: mouse

<400> SEQUENCE: 10

Met Asn Leu Glu Arg Val Ser Asn Glu Glu Lys Leu Asn Leu Cys Arg
 1               5                  10                  15

Lys Tyr Tyr Leu Gly Gly Phe Ala Phe Leu Pro Phe Leu Trp Leu Val
            20                  25                  30

Asn Ile Phe Trp Phe Phe Arg Glu Ala Phe Leu Ala Pro Ala Tyr Thr
        35                  40                  45
```

Glu Gln Ser Gln Ile Lys Gly Tyr Val Trp Arg Ser Ala Val Gly Phe
 50                  55                  60

Leu Phe Trp Val Ile Ile Leu Ala Thr Trp Ile Thr Ile Phe Gln Ile
 65                  70                  75                  80

Tyr Arg Pro Arg Trp Gly Ala Leu Gly Asp Tyr Leu Ser Phe Thr Ile
                 85                  90                  95

Pro Leu Gly Thr Pro
            100

<210> SEQ ID NO 11
<211> LENGTH: 71
<212> TYPE: PRT
<213> ORGANISM: Bos taurus

<400> SEQUENCE: 11

Met Asn Leu Glu Arg Val Ser Asn Glu Glu Lys Leu Asn Leu Cys Arg
 1               5                  10                  15

Lys Tyr Tyr Leu Gly Gly Phe Ala Phe Leu Pro Phe Leu Trp Leu Val
                 20                  25                  30

Asn Ile Phe Trp Phe Phe Arg Glu Ala Phe Ile Val Pro Ala Tyr Thr
                 35                  40                  45

Glu Gln Ser Gln Ile Lys Gly Tyr Val Trp Arg Ser Ala Val Gly Phe
 50                  55                  60

Phe Leu Trp Val Ile Val Leu
 65                  70

<210> SEQ ID NO 12
<211> LENGTH: 101
<212> TYPE: PRT
<213> ORGANISM: human

<400> SEQUENCE: 12

Met Asn Leu Glu Arg Val Ser Asn Glu Glu Lys Leu Asn Leu Cys Arg
 1               5                  10                  15

Lys Tyr Tyr Leu Gly Gly Phe Ala Phe Leu Pro Phe Leu Trp Leu Val
                 20                  25                  30

Asn Ile Phe Trp Phe Phe Arg Glu Ala Phe Leu Val Pro Ala Tyr Thr
                 35                  40                  45

Glu Gln Ser Gln Ile Lys Gly Tyr Val Trp Arg Ser Ala Val Gly Phe
 50                  55                  60

Leu Phe Trp Val Ile Val Leu Thr Ser Trp Ile Thr Ile Phe Gln Ile
 65                  70                  75                  80

Tyr Arg Pro Arg Trp Gly Ala Leu Gly Asp Tyr Leu Ser Phe Thr Ile
                 85                  90                  95

Pro Leu Gly Thr Pro
            100

<210> SEQ ID NO 13
<211> LENGTH: 721
<212> TYPE: PRT
<213> ORGANISM: Caenorhabditis elegans

<400> SEQUENCE: 13

Met Lys Lys Trp Leu Val Ile Val Leu Ile Ile Ala Gly Ile Arg Cys
 1               5                  10                  15

Asp Gly Phe Ser Asp Gln Val Phe Arg Thr Leu Phe Ile Gly Glu Gly
                 20                  25                  30

```
Asn Ala Cys Tyr Arg Thr Phe Asn Lys Thr His Glu Phe Gly Cys Gln
         35                  40                  45

Ala Asn Arg Glu Asn Glu Asn Gly Leu Ile Val Arg Ile Asp Lys Gln
 50                  55                  60

Glu Asp Phe Lys Asn Leu Asp Ser Cys Trp Asn Ser Phe Tyr Pro Lys
 65                  70                  75                  80

Tyr Ser Gly Lys Tyr Trp Ala Leu Leu Pro Val Asn Leu Ile Arg Arg
                 85                  90                  95

Asp Thr Ile Ser Gln Leu Lys Ser Ser Lys Cys Leu Ser Gly Ile Val
                100                 105                 110

Leu Tyr Asn Ser Gly Glu Ser Ile His Pro Gly Asp Glu Ser Thr Ala
            115                 120                 125

Ala Ser His Asp Ala Glu Cys Pro Asn Ala Ala Ser Asp Tyr Tyr Leu
    130                 135                 140

Gln Asp Lys Asn Glu Glu Tyr Cys Glu Arg Lys Ile Asn Ser Arg Gly
145                 150                 155                 160

Ala Ile Thr Arg Asp Gly Leu Met Lys Ile Asp Trp Arg Ile Gln Met
                165                 170                 175

Val Phe Ile Asp Asn Ser Thr Asp Leu Glu Ile Glu Lys Cys Tyr
                180                 185                 190

Ser Met Phe Asn Lys Pro Lys Glu Asp Gly Ser Ser Gly Tyr Pro Tyr
            195                 200                 205

Cys Gly Met Ser Phe Arg Leu Ala Asn Met Ala Ala Gly Asn Ser Glu
    210                 215                 220

Ile Cys Tyr Arg Arg Gly Lys Asn Asp Ala Lys Leu Phe Gln Met Asn
225                 230                 235                 240

Ile Asp Ser Gly Asp Ala Pro Gln Leu Cys Gly Ala Met His Ser Asp
                245                 250                 255

Asn Ile Phe Ala Phe Pro Thr Pro Ile Pro Thr Ser Pro Thr Asn Glu
            260                 265                 270

Thr Ile Ile Thr Ser Lys Tyr Met Met Val Thr Ala Arg Met Asp Ser
        275                 280                 285

Phe Gly Met Ile Pro Glu Ile Ser Val Gly Glu Val Ser Val Leu Thr
    290                 295                 300

Ser Ile Ile Ser Val Leu Ala Ala Ala Arg Ser Met Gly Thr Gln Ile
305                 310                 315                 320

Glu Lys Trp Gln Lys Ala Ser Asn Thr Ser Asn Arg Asn Val Phe Phe
                325                 330                 335

Ala Phe Phe Asn Gly Glu Ser Leu Asp Tyr Ile Gly Ser Gly Ala Ala
            340                 345                 350

Ala Tyr Gln Met Glu Asn Gly Lys Phe Pro Gln Met Ile Arg Ser Asp
        355                 360                 365

Arg Thr His Ile His Pro Ile Arg Pro Asn Glu Leu Asp Tyr Ile Leu
    370                 375                 380

Glu Val Gln Gln Ile Gly Val Ala Lys Gly Arg Lys Tyr Tyr Val His
385                 390                 395                 400

Val Asp Gly Glu Arg Tyr Gln Gln Asn Lys Thr Gln Thr Asp Arg Val
                405                 410                 415

Ile Asp Arg Ile Glu Arg Gly Leu Arg Ser His Ala Phe Asp Leu Glu
            420                 425                 430

Lys Pro Ser Gly Ser Gly Asp Arg Val Pro Pro Ala Ser Trp His Ser
        435                 440                 445

Phe Ala Lys Ala Asp Ala His Val Gln Ser Val Leu Leu Ala Pro Tyr
```

```
            450                 455                 460
Gly Lys Glu Tyr Glu Tyr Gln Arg Val Asn Ser Ile Leu Asp Lys Asn
465                 470                 475                 480

Glu Trp Thr Glu Asp Glu Arg Glu Lys Ala Ile Gln Glu Ile Glu Ala
                485                 490                 495

Val Ser Thr Ala Ile Leu Ala Ala Ala Asp Tyr Val Gly Val Glu
            500                 505                 510

Thr Asp Glu Val Val Ala Lys Val Asp Lys Leu Ile Thr Thr Ile
        515                 520                 525

Phe Asp Cys Leu Ile Thr Ser Asn Phe Trp Phe Asp Cys Asp Phe Met
530                 535                 540

Gln Lys Leu Asp Gly Gly Arg Tyr His Lys Leu Phe Asn Ser Tyr Gly
545                 550                 555                 560

Phe Asn Gln Lys Ser Thr Tyr Ile Ser Met Glu Ser His Thr Ala Phe
                565                 570                 575

Pro Thr Val Leu His Trp Leu Thr Ile Phe Ala Leu Gly Ser Asp Lys
            580                 585                 590

Glu Thr Leu Asn Val Lys Ser Glu Lys Ser Cys Ser His Leu Gly Gln
        595                 600                 605

Phe Gln Ala Met Tyr Thr Tyr Thr Trp Gln Pro Asn Pro Tyr Thr Gly
610                 615                 620

Asn Phe Ser Cys Leu Lys Ser Ala Ile Val Lys Lys Val Met Val Ser
625                 630                 635                 640

Pro Ala Val Asp Ser Gln Thr Pro Glu Glu Met Asn Thr Arg Tyr
                645                 650                 655

Ser Thr Trp Met Glu Ser Val Tyr Ile Ile Glu Ser Val Asn Leu Tyr
            660                 665                 670

Leu Met Glu Asp Ala Ser Phe Glu Tyr Thr Met Ile Leu Ile Ala Val
        675                 680                 685

Ile Ser Ala Leu Leu Ser Ile Phe Ala Val Gly Arg Cys Ser Glu Thr
690                 695                 700

Thr Phe Ile Val Asp Glu Gly Glu Pro Ala Ala Glu Gly Gly Glu Pro
705                 710                 715                 720

Leu

<210> SEQ ID NO 14
<211> LENGTH: 716
<212> TYPE: PRT
<213> ORGANISM: Drosophila melanogaster

<400> SEQUENCE: 14

His Glu Pro Lys Arg Ser His Ala Thr Leu Gln Phe Leu Asp Ala Ile
1               5                   10                  15

Ser Trp Glu Ser Ser Met Glu Met Arg Leu Asn Ala Ala Ser Ile Trp
            20                  25                  30

Leu Leu Ile Leu Ser Tyr Gly Ala Thr Ile Ala Gln Gly Glu Arg Thr
        35                  40                  45

Arg Asp Lys Met Tyr Glu Pro Ile Gly Gly Ala Ser Cys Phe Arg Arg
    50                  55                  60

Leu Asn Gly Thr His Gln Thr Gly Cys Ser Ser Thr Tyr Ser Gly Ser
65                  70                  75                  80

Val Gly Val Leu His Leu Ile Asn Val Glu Ala Asp Leu Glu Phe Leu
                85                  90                  95

Leu Ser Ser Pro Pro Ser Pro Pro Tyr Ala Pro Met Ile Pro Pro His
```

-continued

```
                100                 105                 110
Leu Phe Thr Arg Asn Asn Leu Met Arg Leu Lys Glu Ala Gly Pro Lys
        115                 120                 125
Asn Ile Ser Val Val Leu Leu Ile Asn Arg Thr Asn Gln Met Lys Gln
        130                 135                 140
Phe Ser His Glu Leu Asn Cys Pro Asn Gln Tyr Ser Gly Leu Asn Ser
145                 150                 155                 160
Thr Ser Glu Thr Cys Asp Ala Ser Asn Pro Ala Lys Asn Trp Asn Pro
                165                 170                 175
Trp Gly Thr Gly Leu Leu His Glu Asp Phe Pro Phe Pro Ile Tyr Tyr
        180                 185                 190
Ile Ala Asp Leu Asp Gln Val Thr Lys Leu Glu Lys Cys Phe Gln Asp
        195                 200                 205
Phe Asn Asn His Asn Tyr Glu Thr His Ala Leu Arg Ser Leu Cys Ala
210                 215                 220
Val Glu Val Lys Ser Phe Met Ser Ala Ala Val Asn Thr Glu Val Cys
225                 230                 235                 240
Met Arg Arg Thr Asn Phe Ile Asn Asn Leu Gly Gly Ser Lys Tyr Cys
                245                 250                 255
Asp Pro Leu Glu Gly Arg Asn Val Tyr Ala Thr Leu Tyr Pro Glu Ser
            260                 265                 270
Gln Gln Ser Lys Thr Thr Trp Arg Gln Ser Ile Arg Met Lys Ser Ser
        275                 280                 285
Ile Ser Asn Leu Ser Pro Gly His His His Val Arg Trp Arg Arg
290                 295                 300
Ser Trp Ser His Gly Leu Pro Tyr Gly Ile Cys Trp Phe Gln Leu Ser
305                 310                 315                 320
Val Gly Tyr Leu Leu Lys Gln Leu Leu Pro Pro Gln Ser Lys Asp Leu
                325                 330                 335
His Asn Val Leu Phe Val Thr Phe Asn Gly Glu Ser Tyr Asp Tyr Ile
                340                 345                 350
Gly Ser Gln Arg Phe Val Tyr Asp Met Glu Lys Leu Gln Phe Pro Thr
        355                 360                 365
Glu Ser Thr Gly Thr Pro Pro Ile Ala Phe Asp Asn Ile Asp Phe Met
370                 375                 380
Leu Asp Ile Gly Thr Leu Asp Asp Ile Ser Asn Ile Lys Leu His Ala
385                 390                 395                 400
Leu Asn Gly Thr Thr Leu Ala Gln Gln Ile Leu Glu Arg Leu Asn Asn
                405                 410                 415
Tyr Ala Lys Ser Pro Arg Tyr Gly Phe Asn Leu Asn Ile Gln Ser Glu
                420                 425                 430
Met Ser Ala His Leu Pro Pro Thr Ser Ala Gln Ser Phe Leu Arg Arg
        435                 440                 445
Asp Pro Asn Phe Asn Ala Leu Ile Leu Asn Ala Arg Pro Thr Asn Lys
        450                 455                 460
Tyr Tyr His Ser Ile Tyr Asp Asp Ala Asp Asn Val Asp Phe Thr Tyr
465                 470                 475                 480
Ala Asn Thr Ser Lys Asp Phe Thr Gln Leu Thr Glu Val Asn Asp Phe
                485                 490                 495
Lys Ser Leu Asn Pro Asp Ser Leu Gln Met Lys Val Arg Asn Val Ser
                500                 505                 510
Ser Ile Val Ala Met Ala Leu Tyr Gln Thr Ile Thr Gly Lys Glu Tyr
        515                 520                 525
```

-continued

```
Thr Gly Thr Lys Val Ala Asn Pro Leu Met Ala Asp Glu Phe Leu Tyr
            530                 535                 540

Cys Phe Leu Gln Ser Ala Asp Cys Pro Leu Phe Lys Ala Ala Ser Tyr
545                 550                 555                 560

Pro Gly Ser Gln Leu Thr Asn Leu Pro Pro Met Arg Tyr Ile Ser Val
                565                 570                 575

Leu Gly Gly Ser Gln Glu Ser Ser Gly Tyr Thr Tyr Arg Leu Leu Gly
            580                 585                 590

Tyr Leu Leu Ser Gln Leu Gln Pro Asp Ile His Arg Asp Asn Cys Thr
            595                 600                 605

Asp Leu Pro Leu His Tyr Phe Ala Gly Phe Asn Asn Ile Gly Glu Cys
            610                 615                 620

Arg Leu Thr Thr Gln Asn Tyr Ser His Ala Leu Ser Pro Ala Phe Leu
625                 630                 635                 640

Ile Asp Gly Tyr Asp Trp Ser Ser Gly Met Tyr Ser Thr Trp Ala Glu
                645                 650                 655

Ser Thr Trp Ser Gln Phe Ser Ala Arg Ile Phe Leu Arg Pro Ser Asn
            660                 665                 670

Val His Gln Val Thr Thr Leu Ser Val Gly Ile Val Val Leu Ile Ile
            675                 680                 685

Ser Phe Cys Leu Val Tyr Ile Ile Ser Ser Arg Ser Glu Val Leu Phe
690                 695                 700

Glu Asp Leu Pro Ala Ser Asn Ala Ala Leu Phe Gly
705                 710                 715

<210> SEQ ID NO 15
<211> LENGTH: 708
<212> TYPE: PRT
<213> ORGANISM: human

<400> SEQUENCE: 15

Ala Thr Ala Gly Gly Gly Ser Gly Ala Asp Pro Gly Ser Arg Gly Leu
 1               5                  10                  15

Leu Arg Leu Leu Ser Phe Cys Val Leu Ala Gly Leu Cys Arg Gly
             20                  25                  30

Asn Ser Val Glu Arg Lys Ile Tyr Ile Pro Leu Asn Lys Thr Ala Pro
         35                  40                  45

Cys Val Arg Leu Leu Asn Ala Thr His Gln Ile Gly Cys Gln Ser Ser
     50                  55                  60

Ile Ser Gly Asp Thr Gly Val Ile His Val Val Glu Lys Glu Glu Asp
 65                  70                  75                  80

Leu Gln Trp Val Leu Thr Asp Gly Pro Asn Pro Pro Tyr Met Val Leu
                 85                  90                  95

Leu Glu Ser Lys His Phe Thr Arg Asp Leu Met Glu Lys Leu Lys Gly
            100                 105                 110

Arg Thr Ser Arg Ile Ala Gly Leu Ala Val Ser Leu Thr Lys Pro Ser
        115                 120                 125

Pro Ala Ser Gly Phe Ser Pro Ser Val Gln Cys Pro Asn Asp Gly Phe
    130                 135                 140

Gly Val Tyr Ser Asn Ser Tyr Gly Pro Glu Phe Ala His Cys Arg Glu
145                 150                 155                 160

Ile Gln Trp Asn Ser Leu Gly Asn Gly Leu Ala Tyr Glu Asp Phe Ser
                165                 170                 175

Phe Pro Ile Phe Leu Leu Glu Asp Glu Asn Glu Thr Lys Val Ile Lys
```

-continued

```
            180                 185                 190
Gln Cys Tyr Gln Asp His Asn Leu Ser Gln Asn Gly Ser Ala Pro Thr
            195                 200                 205
Phe Pro Leu Cys Ala Met Gln Leu Phe Ser His Met His Ala Val Ile
210                 215                 220
Ser Thr Ala Thr Cys Met Arg Arg Ser Ser Ile Gln Ser Thr Phe Ser
225                 230                 235                 240
Ile Asn Pro Glu Ile Val Cys Asp Pro Leu Ser Asp Tyr Asn Val Trp
                    245                 250                 255
Ser Met Leu Lys Pro Ile Asn Thr Thr Gly Thr Leu Lys Pro Asp Asp
                260                 265                 270
Arg Val Val Ala Ala Thr Arg Leu Asp Ser Arg Ser Phe Phe Trp
            275                 280                 285
Asn Val Ala Pro Gly Ala Glu Ser Ala Val Ala Ser Phe Val Thr Gln
290                 295                 300
Leu Ala Ala Glu Ala Leu Gln Lys Ala Pro Asp Val Thr Thr Leu
305                 310                 315                 320
Pro Arg Asn Val Met Phe Val Phe Gln Gly Glu Thr Phe Asp Tyr
                    325                 330                 335
Ile Gly Ser Ser Arg Met Val Tyr Asp Met Glu Lys Gly Lys Phe Pro
                340                 345                 350
Val Gln Leu Glu Asn Val Asp Ser Phe Val Glu Leu Gly Gln Val Ala
            355                 360                 365
Leu Arg Thr Ser Leu Glu Leu Trp Met His Thr Asp Pro Val Ser Gln
370                 375                 380
Lys Asn Glu Ser Val Arg Asn Gln Val Glu Asp Leu Leu Ala Thr Leu
385                 390                 395                 400
Glu Lys Ser Gly Ala Gly Val Pro Ala Val Ile Leu Arg Arg Pro Asn
                    405                 410                 415
Gln Ser Gln Pro Leu Pro Ser Ser Leu Gln Arg Phe Leu Arg Ala
                420                 425                 430
Arg Asn Ile Ser Gly Val Val Leu Ala Asp His Ser Gly Ala Phe His
            435                 440                 445
Asn Lys Tyr Tyr Gln Ser Ile Tyr Asp Thr Ala Glu Asn Ile Asn Val
450                 455                 460
Ser Tyr Pro Glu Trp Leu Ser Pro Glu Glu Asp Leu Asn Phe Val Thr
465                 470                 475                 480
Asp Thr Ala Lys Ala Leu Ala Asp Val Ala Thr Val Leu Gly Arg Ala
                    485                 490                 495
Leu Tyr Glu Leu Ala Gly Gly Thr Asn Phe Ser Asp Thr Val Gln Ala
                500                 505                 510
Asp Pro Gln Thr Val Thr Arg Leu Leu Tyr Gly Phe Leu Ile Lys Ala
            515                 520                 525
Asn Asn Ser Trp Phe Gln Ser Ile Leu Arg Gln Asp Leu Arg Ser Tyr
            530                 535                 540
Leu Gly Asp Gly Pro Leu Gln His Tyr Ile Ala Val Ser Ser Pro Thr
545                 550                 555                 560
Asn Thr Thr Tyr Val Val Gln Tyr Ala Leu Ala Asn Leu Thr Gly Thr
                    565                 570                 575
Val Val Asn Leu Thr Arg Glu Gln Cys Gln Asp Pro Ser Lys Val Pro
                580                 585                 590
Ser Glu Asn Lys Asp Leu Tyr Glu Tyr Ser Trp Val Gln Gly Pro Leu
            595                 600                 605
```

```
His Ser Asn Glu Thr Asp Arg Leu Pro Arg Cys Val Arg Ser Thr Ala
    610                 615                 620

Arg Leu Ala Arg Ala Leu Ser Pro Ala Phe Glu Leu Ser Gln Trp Ser
625                 630                 635                 640

Ser Thr Glu Tyr Ser Thr Trp Thr Glu Ser Arg Trp Lys Asp Ile Arg
                645                 650                 655

Ala Arg Ile Phe Leu Ile Ala Ser Lys Glu Leu Glu Leu Ile Thr Leu
                660                 665                 670

Thr Val Gly Phe Gly Ile Leu Ile Phe Ser Leu Ile Val Thr Tyr Cys
                675                 680                 685

Ile Asn Ala Lys Ala Asp Val Leu Phe Ile Ala Pro Arg Glu Pro Gly
    690                 695                 700

Ala Val Ser Tyr
705

<210> SEQ ID NO 16
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 16

Met Ala Ala Ala Val Phe Phe Gly Cys Ala Phe Asp Ala Phe Gly Pro
1               5                   10                  15

Ala Leu Ala Leu Tyr Glu Phe Thr Ile Ala Thr Glu Pro Leu Arg Phe
                20                  25                  30

Ile Phe Leu Ile Ala Gly Ala Phe Phe Gly Leu Val Ser Leu Leu Ile
            35                  40                  45

Ser Ser Leu His Trp Phe Met Ala Arg Val Ile Ile Asp Ile Lys Asp
        50                  55                  60

Gly Pro Thr Gln Lys Tyr Leu Lys Ile Phe Gly Ala Phe Val Ser Val
65                  70                  75                  80

Tyr Leu Gln Glu Met Phe Arg Phe Ala Tyr Tyr Met Leu Leu Lys Lys
                85                  90                  95

Ala Ser Glu Gly Leu Asn Ser Ile Asn Pro Gly Glu Thr Ala Pro Gln
            100                 105                 110

Met Arg Leu Leu Ala Tyr Val Ser Gly Arg Gly Phe Gly Ile Met Ser
        115                 120                 125

Gly Val Phe Thr Phe Val Asn Thr Leu Ser Asp Ser Leu Val Pro Gly
130                 135                 140

Thr Val Gly Ile His Gly Asp Trp Pro Gln Phe Phe Leu Tyr Ser Ala
145                 150                 155                 160

Phe Tyr Thr Leu Val Ile Ile Leu Leu His Val Ala Trp Gly Ile Val
                165                 170                 175

Phe Phe Asp Gly Cys Asp Lys Lys Trp Gly Ile Leu Leu Ile Glu
            180                 185                 190

Leu Leu Thr His Leu Leu Val Ser Ala Phe Thr Phe Ile Ser Ser Tyr
        195                 200                 205

Tyr Gly Ile Gly Leu Ala Ser Ala Phe Ile Ile Leu Val His Met Gly
    210                 215                 220

Thr Trp Ala Phe Leu Ala Ala Ile Gly Ser Cys Arg Ser Leu Lys Leu
225                 230                 235                 240

Cys Lys Leu Cys Gln Asp Lys Asn Phe Leu Leu Leu Asn Gln Arg Ser
```

245 250 255

Arg

<210> SEQ ID NO 17
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 17

Met Thr Asp Ala Val Phe Phe Gly Cys Ala Phe Ile Glu Phe Gly Pro
 1               5                  10                  15

Ala Leu Ala Leu Tyr Val Gly Thr Ile Ala Thr Glu Pro Leu Arg Ile
            20                  25                  30

His Phe Leu Ile Ala Gly Ala Phe Phe Trp Ile Val Ser Leu Leu Ile
        35                  40                  45

Ser Ser Leu Val Lys Phe Met Ala Arg Val Ile Ile Asp Asn Leu Asp
    50                  55                  60

Gly Pro Thr Gln Lys Tyr Leu Leu Met Phe Gly Ala Phe Val Ser Val
 65                  70                  75                  80

Tyr Ile Asn Glu Met Phe Arg Phe Ala Tyr Tyr Lys Gln Leu Lys Lys
                85                  90                  95

Ala Ser Glu Gly Leu Lys Arg Ile Asn Pro Gly Glu Thr Ala Pro Ser
            100                 105                 110

Ser Arg Leu Leu Ala Tyr Val Ser Gly Leu Thr Phe Gly Ile Met Ser
        115                 120                 125

Gly Val Phe Ser Val Val Asn Thr Leu Ser Asp Ser Leu Gly Trp Gly
    130                 135                 140

Thr Val Gly Ile His Gly Asp Ser Tyr Gln Phe Phe Leu Tyr Ser Ala
145                 150                 155                 160

Phe Met Ala Leu Val Ile Ile Leu Leu His Val Phe Asp Gly Ile Val
                165                 170                 175

Phe Phe Asp Gly Cys Glu Glu Lys Lys Trp Gly Ile Leu Leu Ile Val
            180                 185                 190

Phe Leu Thr His Leu Leu Val Ser Ala Gln Gly Phe Ile Ser Ser Tyr
        195                 200                 205

Tyr Gly Ile Asn His Ala Ser Ala Phe Ile Ile Leu Val Leu Ile Gly
    210                 215                 220

Thr Trp Ala Phe Leu Ala Ala Gly Lys Ser Cys Arg Ser Leu Lys Leu
225                 230                 235                 240

Cys Leu Met Cys Gln Asp Lys Asn Phe Leu Leu Tyr Gln Gln Arg Ser
                245                 250                 255

Arg

<210> SEQ ID NO 18
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 18

Met Thr Ala Asp Val Phe Phe Gly Cys Ala Phe Ile Ala Glu Gly Pro
 1               5                  10                  15

```
Ala Leu Ala Leu Tyr Val Phe Phe Ile Ala Thr Glu Pro Leu Arg Ile
            20                  25                  30

Ile Gly Leu Ile Ala Gly Ala Phe Phe Trp Leu His Ser Leu Leu Ile
        35                  40                  45

Ser Ser Leu Val Trp Ile Met Ala Arg Val Ile Ile Asp Asn Lys Lys
    50                  55                  60

Gly Pro Thr Gln Lys Tyr Leu Leu Ile Leu Gly Ala Phe Val Ser Val
65                  70                  75                  80

Tyr Ile Gln Met Met Phe Arg Phe Ala Tyr Tyr Lys Leu Asn Lys Lys
                85                  90                  95

Ala Ser Glu Gly Leu Lys Ser Gln Asn Pro Gly Glu Thr Ala Pro Ser
            100                 105                 110

Met Ser Leu Leu Ala Tyr Val Ser Gly Leu Gly Thr Gly Ile Met Ser
        115                 120                 125

Gly Val Phe Ser Phe Trp Asn Thr Leu Ser Asp Ser Leu Gly Pro Tyr
    130                 135                 140

Thr Val Gly Ile His Gly Asp Ser Pro Ala Phe Phe Leu Tyr Ser Ala
145                 150                 155                 160

Phe Met Thr Asp Val Ile Ile Leu Leu His Val Phe Trp Glu Ile Val
                165                 170                 175

Phe Phe Asp Gly Cys Glu Lys Phe Lys Trp Gly Ile Leu Leu Ile Val
            180                 185                 190

Leu Gly Thr His Leu Leu Val Ser Ala Gln Thr His Ile Ser Ser Tyr
        195                 200                 205

Tyr Gly Ile Asn Leu Ile Ser Ala Phe Ile Ile Leu Val Leu Met Lys
    210                 215                 220

Thr Trp Ala Phe Leu Ala Ala Gly Gly Leu Cys Arg Ser Leu Lys Leu
225                 230                 235                 240

Cys Leu Leu Met Gln Asp Lys Asn Phe Leu Tyr Asn Asn Arg Ser
                245                 250                 255

Arg

<210> SEQ ID NO 19
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 19

Met Thr Ala Ala Ala Phe Phe Gly Cys Ala Phe Ile Ala Phe Asp Pro
1               5                   10                  15

Ala Leu Ala Leu Tyr Val Phe Thr Glu Ala Thr Glu Pro Leu Arg Ile
            20                  25                  30

Ile Phe Phe Ile Ala Gly Ala Phe Phe Trp Leu Val Gly Leu Leu Ile
        35                  40                  45

Ser Ser Leu Val Trp Phe His Ala Arg Val Ile Ile Asp Asn Lys Asp
    50                  55                  60

Ile Pro Thr Gln Lys Tyr Leu Leu Ile Phe Lys Ala Phe Val Ser Val
65                  70                  75                  80

Tyr Ile Gln Glu Leu Phe Arg Phe Ala Tyr Tyr Lys Leu Leu Met Lys
                85                  90                  95

Ala Ser Glu Gly Leu Lys Ser Ile Gln Pro Gly Glu Thr Ala Pro Ser
            100                 105                 110
```

```
Met Arg Arg Leu Ala Tyr Val Ser Gly Leu Gly Phe Ser Ile Met Ser
            115                 120                 125

Gly Val Phe Ser Phe Val Thr Thr Leu Ser Asp Ser Leu Gly Pro Gly
        130                 135                 140

Val Val Gly Ile His Gly Asp Ser Pro Gln Trp Phe Leu Tyr Ser Ala
145                 150                 155                 160

Phe Met Thr Leu Tyr Ile Ile Leu Leu His Val Phe Trp Gly Ala Val
                165                 170                 175

Phe Phe Asp Gly Cys Glu Lys Lys Asp Trp Gly Ile Leu Leu Ile Val
            180                 185                 190

Leu Leu Glu His Leu Val Ser Ala Gln Thr Phe Ser Ser Tyr
            195                 200                 205

Tyr Gly Ile Asn Leu Ala Gly Ala Phe Ile Ile Leu Val Leu Met Gly
        210                 215                 220

His Trp Ala Phe Leu Ala Ala Gly Gly Ser Ile Arg Ser Leu Lys Leu
225                 230                 235                 240

Cys Leu Leu Cys Lys Asp Lys Asn Phe Leu Leu Tyr Asn Gln Leu Ser
                245                 250                 255

Arg

<210> SEQ ID NO 20
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 20

Met Thr Ala Ala Val Ala Phe Gly Cys Ala Phe Ile Ala Phe Gly Asp
  1               5                  10                  15

Ala Leu Ala Leu Tyr Val Phe Thr Ile Glu Thr Glu Pro Leu Arg Ile
             20                  25                  30

Ile Phe Leu Phe Ala Gly Ala Phe Phe Trp Leu Val Ser Gly Leu Ile
         35                  40                  45

Ser Ser Leu Val Trp Phe Met His Arg Val Ile Ile Asp Asn Lys Asp
     50                  55                  60

Gly Ile Thr Gln Lys Tyr Leu Leu Ile Phe Gly Lys Phe Val Ser Val
 65                  70                  75                  80

Tyr Ile Gln Glu Met Leu Arg Phe Ala Tyr Tyr Lys Leu Leu Lys Met
                 85                  90                  95

Ala Ser Glu Gly Leu Lys Ser Ile Asn Asn Gly Glu Thr Ala Pro Ser
            100                 105                 110

Met Arg Leu Gln Ala Tyr Val Ser Gly Leu Gly Phe Gly Arg Met Ser
            115                 120                 125

Gly Val Phe Ser Phe Val Asn Ser Leu Ser Asp Ser Leu Gly Pro Gly
        130                 135                 140

Thr Thr Gly Ile His Gly Asp Ser Pro Gln Phe Val Leu Tyr Ser Ala
145                 150                 155                 160

Phe Met Thr Leu Val Trp Ile Leu Leu His Val Phe Trp Gly Ile Tyr
                165                 170                 175

Phe Phe Asp Gly Cys Glu Lys Lys Lys Ala Gly Ile Leu Leu Ile Val
            180                 185                 190

Leu Leu Thr Asp Leu Leu Val Ser Ala Gln Thr Phe Ile Glu Ser Tyr
            195                 200                 205
```

-continued

```
Tyr Gly Ile Asn Leu Ala Ser Phe Phe Ile Ile Leu Val Leu Met Gly
        210                 215                 220
Thr Gly Ala Phe Leu Ala Ala Gly Gly Ser Cys His Ser Leu Lys Leu
225                 230                 235                 240
Cys Leu Leu Cys Gln Ile Lys Asn Phe Leu Leu Tyr Asn Gln Arg Lys
                245                 250                 255
Arg

<210> SEQ ID NO 21
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 21

Met Thr Ala Ala Val Phe Ala Gly Cys Ala Phe Ile Ala Phe Gly Pro
1               5                   10                  15
Asp Leu Ala Leu Tyr Val Phe Thr Ile Ala Glu Glu Pro Leu Arg Ile
                20                  25                  30
Ile Phe Leu Ile Phe Gly Ala Phe Phe Trp Leu Val Ser Leu Gly Ile
            35                  40                  45
Ser Ser Leu Val Trp Phe Met Ala His Val Ile Asp Asn Lys Asp
        50                  55                  60
Gly Pro Ile Gln Lys Tyr Leu Leu Ile Phe Gly Ala Lys Val Ser Val
65                  70                  75                  80
Tyr Ile Gln Glu Met Phe Leu Phe Ala Tyr Tyr Lys Leu Leu Lys Lys
                85                  90                  95
Met Ser Glu Gly Leu Lys Ser Ile Asn Pro Asn Glu Thr Ala Pro Ser
                100                 105                 110
Met Arg Leu Leu Gln Tyr Val Ser Gly Leu Gly Phe Gly Ile Arg Ser
            115                 120                 125
Gly Val Phe Ser Phe Val Asn Thr Ser Ser Asp Ser Leu Gly Pro Gly
        130                 135                 140
Thr Val Thr Ile His Gly Asp Ser Pro Gln Phe Phe Val Tyr Ser Ala
145                 150                 155                 160
Phe Met Thr Leu Val Ile Trp Leu Leu His Val Phe Trp Gly Ile Val
                165                 170                 175
Tyr Phe Asp Gly Cys Glu Lys Lys Lys Trp Ala Ile Leu Leu Ile Val
                180                 185                 190
Leu Leu Thr His Asp Leu Val Ser Ala Gln Thr Phe Ile Ser Glu Tyr
            195                 200                 205
Tyr Gly Ile Asn Leu Ala Ser Ala Gly Ile Ile Leu Val Leu Met Gly
        210                 215                 220
Thr Trp His Phe Leu Ala Ala Gly Gly Ser Cys Arg Ile Leu Lys Leu
225                 230                 235                 240
Cys Leu Leu Cys Gln Asp Leu Asn Phe Leu Leu Tyr Asn Gln Arg Ser
                245                 250                 255
Met

<210> SEQ ID NO 22
<211> LENGTH: 257
<212> TYPE: PRT
<213> ORGANISM: Artificial Sequence
<220> FEATURE:
<223> OTHER INFORMATION: Description of Artificial Sequence: Synthetic
```

-continued

Sequence

<400> SEQUENCE: 22

Met Thr Ala Ala Val Phe Phe Ala Cys Ala Phe Ile Ala Phe Gly Pro
1               5                   10                  15

Ala Asp Ala Leu Tyr Val Phe Thr Ile Ala Thr Phe Pro Leu Arg Ile
                20                  25                  30

Ile Phe Leu Ile Ala His Ala Phe Phe Trp Leu Val Ser Leu Leu Lys
            35                  40                  45

Ser Ser Leu Val Trp Phe Met Ala Arg Leu Ile Ile Asp Asn Lys Asp
        50                  55                  60

Gly Pro Thr Met Lys Tyr Leu Leu Ile Phe Gly Ala Phe Asn Ser Val
65                  70                  75                  80

Tyr Ile Gln Glu Met Phe Arg Gln Ala Tyr Tyr Lys Leu Leu Lys Lys
                85                  90                  95

Ala Arg Glu Gly Leu Lys Ser Ile Asn Pro Gly Ser Thr Ala Pro Ser
            100                 105                 110

Met Arg Leu Leu Ala Thr Val Ser Gly Leu Gly Phe Gly Ile Met Val
        115                 120                 125

Gly Val Phe Ser Phe Val Asn Thr Leu Trp Asp Ser Leu Gly Pro Gly
130                 135                 140

Thr Val Gly Tyr His Gly Asp Ser Pro Gln Phe Phe Leu Ala Ser Ala
145                 150                 155                 160

Phe Met Thr Leu Val Ile Ile Asp Leu His Val Phe Trp Gly Ile Val
                165                 170                 175

Phe Glu Asp Gly Cys Glu Lys Lys Lys Trp Gly Phe Leu Leu Ile Val
            180                 185                 190

Leu Leu Thr His Leu Gly Val Ser Ala Gln Thr Phe Ile Ser Ser His
        195                 200                 205

Tyr Gly Ile Asn Leu Ala Ser Ala Phe Lys Ile Leu Val Leu Met Gly
210                 215                 220

Thr Trp Ala Leu Leu Ala Ala Gly Gly Ser Cys Arg Ser Met Lys Leu
225                 230                 235                 240

Cys Leu Leu Cys Gln Asp Lys Gln Phe Leu Leu Tyr Asn Gln Arg Ser
                245                 250                 255

Arg

<210> SEQ ID NO 23
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 23

Met Thr Ala Ala Val Phe Phe Gly Ala Ala Phe Ile Ala Phe Gly Pro
1               5                   10                  15

Ala Leu Asp Leu Tyr Val Phe Thr Ile Ala Thr Glu Glu Leu Arg Ile
                20                  25                  30

Ile Phe Leu Ile Ala Gly Phe Phe Trp Leu Val Ser Leu Leu Ile
            35                  40                  45

Gly Ser Leu Val Trp Phe Met Ala Arg Val His Ile Asp Asn Lys Asp
        50                  55                  60

Gly Pro Thr Gln Ile Tyr Leu Leu Ile Phe Gly Ala Phe Val Lys Val
65                  70                  75                  80

```
Tyr Ile Gln Glu Met Phe Arg Phe Leu Tyr Lys Leu Leu Lys Lys
                85                  90                  95

Ala Ser Met Gly Leu Lys Ser Ile Asn Pro Gly Glu Asn Ala Pro Ser
            100                 105                 110

Met Arg Leu Leu Ala Tyr Gln Ser Gly Leu Gly Phe Gly Ile Met Ser
        115                 120                 125

Arg Val Phe Ser Phe Val Asn Thr Leu Ser Ser Leu Gly Pro Gly
130                 135                 140

Thr Val Gly Ile Thr Gly Asp Ser Pro Gln Phe Phe Leu Tyr Val Ala
145                 150                 155                 160

Phe Met Thr Leu Val Ile Ile Leu Trp His Val Phe Trp Gly Ile Val
                165                 170                 175

Phe Phe Tyr Gly Cys Glu Lys Lys Trp Gly Ile Ala Leu Ile Val
            180                 185                 190

Leu Leu Thr His Leu Leu Asp Ser Ala Gln Thr Phe Ile Ser Ser Tyr
        195                 200                 205

Glu Gly Ile Asn Leu Ala Ser Ala Phe Ile Phe Leu Val Leu Met Gly
    210                 215                 220

Thr Trp Ala Phe Gly Ala Ala Gly Gly Ser Cys Arg Ser Leu His Leu
225                 230                 235                 240

Cys Leu Leu Cys Gln Asp Lys Asn Ile Leu Leu Tyr Asn Gln Arg Ser
                245                 250                 255

Arg

<210> SEQ ID NO 24
<211> LENGTH: 257
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 24

Met Thr Ala Ala Val Phe Phe Gly Cys Asp Phe Ile Ala Phe Gly Pro
1               5                   10                  15

Ala Leu Ala Glu Tyr Val Phe Thr Ile Ala Thr Glu Pro Phe Arg Ile
            20                  25                  30

Ile Phe Leu Ile Ala Gly Ala Gly Phe Trp Leu Val Ser Leu Leu Ile
        35                  40                  45

Ser His Leu Val Trp Phe Met Ala Arg Val Ile Lys Asp Asn Lys Asp
    50                  55                  60

Gly Pro Thr Gln Lys Leu Leu Ile Phe Gly Ala Phe Val Ser Met
65                  70                  75                  80

Tyr Ile Gln Glu Met Phe Arg Phe Ala Asn Tyr Lys Leu Leu Lys Lys
                85                  90                  95

Ala Ser Glu Gln Leu Lys Ser Ile Asn Pro Gly Glu Thr Arg Pro Ser
            100                 105                 110

Met Arg Leu Leu Ala Tyr Val Thr Gly Leu Gly Phe Gly Ile Met Ser
        115                 120                 125

Gly Trp Phe Ser Phe Val Asn Thr Leu Ser Asp Tyr Leu Gly Pro Gly
    130                 135                 140

Thr Val Gly Ile His Ala Asp Ser Pro Gln Phe Phe Leu Tyr Ser Asp
145                 150                 155                 160

Phe Met Thr Leu Val Ile Ile Leu Leu Glu Val Phe Trp Gly Ile Val
                165                 170                 175
```

-continued

```
Phe Phe Asp Phe Cys Glu Lys Lys Lys Trp Gly Ile Leu Gly Ile Val
            180                 185                 190

Leu Leu Thr His Leu Leu Val His Ala Gln Thr Phe Ile Ser Ser Tyr
        195                 200                 205

Tyr Ile Ile Asn Leu Ala Ser Ala Phe Ile Ile Lys Val Leu Met Gly
    210                 215                 220

Thr Trp Ala Phe Leu Leu Ala Gly Gly Ser Cys Arg Ser Leu Lys Met
225                 230                 235                 240

Cys Leu Leu Cys Gln Asp Lys Asn Phe Asn Leu Tyr Asn Gln Arg Ser
                245                 250                 255

Arg

<210> SEQ ID NO 25
<211> LENGTH: 925
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 25

Gly Ala Thr Gly Ala Cys Thr Gly Cys Gly Gly Cys Cys Gly Thr Gly
  1               5                  10                  15

Thr Thr Cys Thr Thr Cys Gly Gly Cys Thr Gly Cys Gly Cys Cys Thr
            20                  25                  30

Thr Cys Ala Thr Thr Gly Cys Cys Thr Thr Cys Gly Gly Gly Cys Cys
        35                  40                  45

Thr Gly Cys Gly Cys Thr Cys Gly Cys Cys Cys Thr Thr Thr Ala Thr
    50                  55                  60

Gly Thr Cys Thr Thr Cys Ala Cys Cys Ala Thr Cys Gly Cys Cys Ala
 65                  70                  75                  80

Cys Cys Gly Ala Gly Cys Cys Gly Thr Thr Gly Cys Gly Thr Ala Thr
                85                  90                  95

Cys Ala Thr Cys Thr Thr Cys Cys Thr Cys Ala Thr Cys Gly Cys Cys
            100                 105                 110

Gly Gly Ala Gly Cys Thr Thr Thr Cys Thr Thr Cys Thr Gly Gly Thr
        115                 120                 125

Thr Gly Gly Thr Gly Thr Cys Thr Cys Thr Ala Cys Thr Gly Ala Thr
    130                 135                 140

Thr Thr Cys Gly Thr Cys Cys Cys Thr Thr Gly Thr Thr Thr Gly Gly
145                 150                 155                 160

Thr Thr Cys Ala Thr Gly Gly Cys Ala Ala Gly Ala Gly Thr Cys Ala
                165                 170                 175

Thr Thr Ala Thr Thr Gly Ala Cys Ala Ala Cys Ala Ala Ala Gly Ala
            180                 185                 190

Thr Gly Gly Ala Cys Cys Ala Ala Cys Ala Cys Ala Gly Ala Ala Ala
        195                 200                 205

Thr Ala Thr Cys Thr Gly Cys Thr Gly Ala Thr Cys Thr Thr Thr Gly
    210                 215                 220

Gly Ala Gly Cys Gly Thr Thr Thr Gly Thr Cys Thr Cys Thr Gly Thr
225                 230                 235                 240

Cys Thr Ala Thr Ala Thr Cys Cys Ala Ala Gly Ala Ala Ala Thr Gly
                245                 250                 255

Thr Thr Cys Cys Gly Ala Thr Thr Thr Gly Cys Ala Thr Ala Thr Thr
            260                 265                 270
```

```
Ala Thr Ala Ala Ala Cys Thr Cys Thr Thr Ala Ala Ala Ala Ala
            275                 280                 285
Ala Gly Cys Cys Ala Gly Thr Gly Ala Ala Gly Gly Thr Thr Thr Gly
        290                 295                 300
Ala Ala Gly Ala Gly Thr Ala Thr Ala Ala Cys Cys Cys Ala Gly
305                 310                 315                 320
Gly Thr Gly Ala Gly Ala Cys Ala Gly Cys Ala Cys Cys Thr Cys
                325                 330                 335
Thr Ala Thr Gly Cys Gly Ala Cys Thr Gly Cys Thr Gly Cys Cys
            340                 345                 350
Thr Ala Thr Gly Thr Thr Thr Cys Thr Gly Gly Cys Thr Thr Gly Gly
            355                 360                 365
Gly Cys Thr Thr Thr Gly Gly Ala Ala Thr Cys Ala Thr Gly Ala Gly
        370                 375                 380
Thr Gly Gly Ala Gly Thr Ala Thr Thr Thr Cys Cys Thr Thr Thr
385                 390                 395                 400
Gly Thr Gly Ala Ala Thr Ala Cys Cys Thr Ala Thr Cys Thr Gly
                405                 410                 415
Ala Cys Thr Cys Cys Thr Thr Gly Gly Gly Cys Cys Ala Gly Gly
            420                 425                 430
Cys Ala Cys Ala Gly Thr Gly Gly Gly Cys Ala Thr Thr Cys Ala Thr
            435                 440                 445
Gly Gly Ala Gly Ala Thr Thr Cys Thr Cys Thr Cys Ala Ala Thr
        450                 455                 460
Thr Cys Thr Thr Cys Cys Thr Thr Ala Thr Thr Cys Ala Gly Cys
465                 470                 475                 480
Thr Thr Thr Cys Ala Thr Gly Ala Cys Gly Cys Thr Gly Gly Thr Cys
                485                 490                 495
Ala Thr Thr Ala Thr Cys Thr Gly Cys Thr Gly Cys Ala Thr Gly
            500                 505                 510
Thr Ala Thr Thr Cys Thr Gly Gly Gly Gly Cys Ala Thr Thr Gly Thr
            515                 520                 525
Ala Thr Thr Thr Thr Thr Thr Gly Ala Thr Gly Gly Cys Thr Gly Thr
530                 535                 540
Gly Ala Gly Ala Ala Gly Ala Ala Ala Ala Gly Thr Gly Gly Gly
545                 550                 555                 560
Gly Cys Ala Thr Cys Cys Thr Cys Cys Thr Thr Ala Thr Cys Gly Thr
                565                 570                 575
Thr Cys Thr Cys Cys Thr Gly Ala Cys Cys Cys Ala Cys Cys Thr Gly
            580                 585                 590
Cys Thr Gly Gly Thr Gly Thr Cys Ala Gly Cys Cys Cys Ala Gly Ala
            595                 600                 605
Cys Cys Thr Thr Cys Ala Thr Ala Ala Gly Thr Cys Thr Thr Ala
        610                 615                 620
Thr Thr Ala Thr Gly Gly Ala Ala Thr Ala Ala Cys Cys Thr Gly
625                 630                 635                 640
Gly Cys Gly Thr Cys Ala Gly Cys Ala Thr Thr Ala Thr Ala Ala
                645                 650                 655
Thr Cys Cys Thr Gly Gly Thr Gly Cys Thr Cys Ala Thr Gly Gly Gly
            660                 665                 670
Cys Ala Cys Cys Thr Gly Gly Gly Cys Ala Thr Thr Cys Thr Ala
            675                 680                 685
```

```
Gly Cys Thr Gly Cys Gly Gly Ala Gly Gly Cys Ala Gly Cys Thr
        690                 695                 700
Gly Cys Cys Gly Ala Ala Gly Cys Cys Thr Gly Ala Ala Cys Thr
705                 710                 715                 720
Cys Thr Gly Cys Cys Thr Gly Cys Thr Gly Cys Cys Ala Ala
            725                 730                 735
Gly Ala Cys Ala Ala Gly Ala Ala Cys Thr Thr Thr Cys Thr Thr
        740                 745                 750
Thr Thr Thr Ala Cys Ala Ala Cys Cys Ala Gly Cys Gly Cys Thr
        755                 760                 765
Cys Cys Ala Gly Ala Thr Ala Ala Cys Cys Thr Cys Ala Gly Gly Ala
        770                 775                 780
Ala Cys Cys Ala Gly Cys Ala Cys Thr Thr Cys Cys Ala Ala Ala
785                 790                 795                 800
Cys Cys Gly Cys Ala Gly Ala Cys Thr Ala Cys Ala Thr Cys Thr Thr
        805                 810                 815
Thr Ala Gly Ala Gly Gly Ala Ala Gly Cys Ala Cys Ala Ala Cys Thr
        820                 825                 830
Gly Thr Gly Cys Cys Thr Thr Thr Thr Cys Thr Gly Ala Ala Ala
        835                 840                 845
Ala Thr Cys Cys Thr Thr Thr Thr Thr Cys Thr Gly Gly Thr Gly
850                 855                 860
Gly Ala Ala Thr Thr Gly Ala Gly Ala Ala Gly Ala Ala Ala Thr
865                 870                 875                 880
Ala Ala Ala Ala Cys Thr Ala Thr Gly Cys Ala Gly Ala Thr Ala Thr
            885                 890                 895
Gly Cys Gly Thr Thr Cys Cys Ala Ala Ala Ala Ala Ala Ala Ala
        900                 905                 910
Ala Ala Ala Ala Ala Ala Ala Ala Ala Ala Ala
        915                 920                 925
```

<210> SEQ ID NO 26
<211> LENGTH: 925
<212> TYPE: DNA
<213> ORGANISM: human

<400> SEQUENCE: 26

```
gatgactgcg gccgtgttct tcggctgcgc cttcattgcc ttcgggcctg cgctcgccct    60
ttatgtcttc accatcgcca ccgagccgtt gcgtatcatc ttcctcatcg ccggagcttt   120
cttctggttg gtgtctctac tgatttcgtc ccttgtttgg ttcatggcaa gagtcattat   180
tgacaacaaa gatggaccaa cacagaaata tctgctgatc tttggagcgt ttgtctctgt   240
ctatatccaa gaaatgttcc gatttgcata ttataaactc ttaaaaaaag ccagtgaagg   300
tttgaagagt ataaacccag gtgagacagc accctctatg cgactgctgg cctatgtttc   360
tggcttgggc tttggaatca tgagtggagt attttccttt gtgaataccc tatctgactc   420
cttgggccca ggcacagtgg gcattcatgg agattctcct caattcttcc tttattcagc   480
tttcatgacg ctggtcatta tcttgctgca tgtattctgg ggcattgtat tttttgatgg   540
ctgtgagaag aaaaagtggg gcatcctcct tatcgttctc ctgacccacc tgctggtgtc   600
agcccagacc ttcataagtt cttattatgg aataaacctg cgtcagcat ttataatcct   660
ggtgctcatg ggcaccctggg cattcttagc tgcgggaggc agctgccgaa gcctgaaact   720
ctgcctgctc tgccaagaca agaactttct tctttacaac cagcgctcca gataacctca   780
```

```
gggaaccagc acttcccaaa ccgcagacta catctttaga ggaagcacaa ctgtgccttt      840
ttctgaaaat ccctttttct ggtggaattg agaaagaaat aaaactatgc agatatgcgt      900
tccaaaaaaa aaaaaaaaaa aaaaa                                            925
```

<210> SEQ ID NO 27
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 27

```
gatgacagcg gccgttttct tcggctgcgc cttgattgcc ttagggcctg ctctcgccct      60
ctatgtcttg accatcgcaa ccgagccttt gcgtatcatc ttcctgatcg ccggagcttt     120
cttttggttg gtctctctac tgatttcgtc acttgtttgt ttcatggcca gagtcatgat     180
tgacaaaaaa gatggtccaa cacacaaata tctgctgatc ttaggagcgt ttgtctctgt     240
ctatatccag gaaatgttac gatttgctta ttataacctc ttaaagaaag ccagagaagg     300
ttttaagagt atcaacccag gggagacagc accctctatt cgactgctcg cctatgtgtc     360
tggcttaggc tttggtatca tgagcggagt attgtccttt gtaaatacco tgtctgactc     420 cttgggggccg ggcacagtag gcattcaggg agattcccct caattgttcc tttaatcagc     480
ttttatgacg ctcgtcatta tgttgctgca agtattctgt ggcattgtct ttttgaggg      540 ctgtgaaaag aaaaattggg gcatcctcct tatggttctc ctaacccacc ttctggtgtc     600
cgcccagacg ttcataagat cttattatgg aataaacctg gcgtcggcat ttataatcct     660
ggttctcatg gcacctggg cgttcttagc agcgggaggt agctgccgca gcctgaagct      720
ctgcctactc tgccatgaca agaactttct tctgtacaac caacgctcca gttaacctca     780
cggaaccagg acttcccaaa ccgcagatta catcttcaga ggaaggacaa ctgtaccttt     840
ttctgaaaat ccctttttct ggtggaattg agaaagaaat aaaactatcc agatatgggt     900
tccaaaaaaa aaaaataaaa aaaac                                            925
```

<210> SEQ ID NO 28
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 28

```
gatgactgcg gccgtcttct tcgggtgcgc cttaattgcc tttgggcctg ccctcgccct      60
gtatgtctta accatcgcta ccgagcccct gcgtatgatc ttcctaatcg ccggtgcttt     120
cttctggttg gtgtctctac taatttcgtc tcttgtttgc ttcatggcga gagtcataat     180
tgacaataaa gatggcccaa cacagaaata tctactgatc tttggagcgt tcgtctctgt     240
gtatatccaa gaaatgtttc gatttgccta ttataagctc ttaaaaaaag ccagtgaagg     300
tttcaagagt atgaacccag gagagacagc tccctctatc cgactgctgg cctatgtatc     360
tggctttggc tttggcatca tgaggggagt attatccttt gttaataccc tctctgactc     420
gttggggcca ggcacagttg gcattcacgg agattcgcct caattattcc tttattcagc     480
tttcatgacg ctggtcatta tattgctgca tgtattctgc ggcattgtgt tttttgaagg     540
ctgtgataag aaaaactggg gcatgctcct tatagttctc cttacccacc tcctggtgtc     600
```

```
ggcccagaca ttcataagtt cttattacgg aataaagctg gcgtcagcat ttattatcct      660
ggtcctcatg gggacctggg cattcttagc tgcgggaggc agctgccgga gcctgaaact      720
ctgccttctc tgccacgaca agaagtttct tctatacaac catcgctcca gctaacctca      780
gggaaccaga acttcccata ccgcagacta catcttgaga ggaagaacaa ctgttccttt      840
ttccgaaaat ccgttttcct gatggaattg tgaaagaaac aaaactatgc agatatgagt      900
tccaaataaa aaaacaaaa aaaag                                             925
```

<210> SEQ ID NO 29  
<211> LENGTH: 925  
<212> TYPE: DNA  
<213> ORGANISM: Artificial Sequence  
<220> FEATURE:  
<223> OTHER INFORMATION: Description of Artificial Sequence: Synthetic  
Sequence <400> SEQUENCE: 29

```
gatgaccgcg gccgtgttct tcggatgcgc ctttattgcc ttcgggcctg cgctcgccct       60
atatgtcttt accatcgcca ccgagccgtt gcgtataatc ttccttatcg ccggcgcttt      120
cttgtggttg gtatctctac ttatttcgtc ccttgtttgg ttcatggcaa gagtcattat      180
tgacaacaaa gatgggccaa cacaaaaata tcttctgatc ttcggagcgt tggtctctgt      240
atatatccat gaaatgttcc gatttgcgta ttataaactc ttaaataaag ccagcgaagg      300
tttgaagagt ataaacccag gtgagacagc cccctctatg cgactgctag cctatgtttc      360
tggcttcggc tttgggatca tgagaggagt attttccttt gtcaatacc tgtctgactc       420 attgggcct ggcacagtcg gcattcaggg agattcacct caattttcc tttactcagc        480 tttgatgacg ctagtcatta ttttgctgca cgtattctgg ggcattgtat tttttgatgg      540
ctgtgacaag aaaaagtggg gcatactcct tattgttctc ctcacccacc tgctggtgtc      600
agcccagact ttcataagct cttattaggg aataaaactg gcgtctgcat ttatcatcct      660
ggtgctcatg ggaacctggg cttcttagc cgcgggaggg agctgccgaa gcctgaatct      720
ctgcctcctc tgccaggaca agaaatttct tctttacaac caccgctcca ggtaacctca      780
aggaaccagt acttcccaca ccgcagagta catcttaaga ggaagtacaa ctgtcccttt      840
ttcggaaaat ccattttct gttggaattg cgaaagaaag aaaactatac agatatgtgt       900
tccaaacaaa aaaagaaaa aaaaa                                             925
```

<210> SEQ ID NO 30  
<211> LENGTH: 925  
<212> TYPE: DNA  
<213> ORGANISM: Artificial Sequence  
<220> FEATURE:  
<223> OTHER INFORMATION: Description of Artificial Sequence: Synthetic  
Sequence <400> SEQUENCE: 30

```
gatgacggcg gccgtattct tcggttgcgc cttcattgcc ttggggcctg cactcgccct       60
ttatgtcttc accatcgcga ccgagccatt gcgtattatc ttcctcatcg ccggggcttt      120
cttatggttg gtttctctac tcatttcgtc gcttgtttga ttcatggcta gagtcatcat      180
tgacaagaaa gatggaccaa cacataaata tctcctgatc ttgggagcgt tagtctctgt      240
ttatatccac gaaatgttgc gatttgcata ttataatctc ttaaacaaag ccagggaagg      300
tttaaagagt attaacccag gcgagacagc gccctctata cgactgcttg cctatgtctc      360
```

```
tggcttgggc tttggaatca tgagtggagt attctccttt gtgataccc  tatctgactc      420
tttgggccc  ggcacagtgg gcattcaagg agattctcct caattcttcc tttagtcagc      480
tttaatgacg cttgtcatta tcttgctgca ggtattctga ggcattgttt ttttttgacgg     540
ctgtgagaag aaaaaatggg gcattctcct tatcgttctc ctgacccacc tactggtgtc      600
tgcccagacc ttcataaggt cttattaagg aataaatctg gcgtccgcat ttatgatcct      660
ggtactcatg ggtacctggg ccttcttagc ggcgggagga agctgccgta gcctgaacct      720
ctgcctgctc tgccaagaca agaattttct tctctacaac cagcgctcca gataacctca      780
tggaaccagc acttcccaga ccgcagaata catcttttaga ggaagcacaa ctgtgccttt     840
ttcagaaaat cctttttttct gctggaattg ggaagaaaa  aaaactattc agatatgcgt     900
tccaaagaaa aaaaaaaaa  aaaat                                            925

<210> SEQ ID NO 31
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 31
gatgactgca gccgtgtttt tcggctgcgc cttcatggcc ttcggacctg cgcttgccct       60
ttacgtcttc acgatcgcca cagagccgtt tcgtatcatc ttcctcatgg ccggagcatt      120
cttctgtttg gtgtccctac tgatgtcgtc cctagtttgg tttatggcaa gcgtcattat      180
ggacaacaaa gatggaccta cacagaacta tctgctgatc tttggagcgt ttgtttctgt      240
ctacatccaa gagatgttcc gatttgcata ttataaactc ttaaaaaagg ccagtgaagg      300
tttgaatagt ataaacccag gtgagacagc accatctatg cgtctgctgg cctatgtttc      360
gggcttggga tttggaatta tgagtggcgt attttcgttt gtgaaaaccc tatctgactc      420
cttcgggcca gggacagtgg gaattcatgg tgattctccc caattcttgc tttattcagc      480
tttcattacg ctggtcatta tcttgctgca tgtattctgg ggtattgtat tctttgatgg      540
gtgtgagaaa aaaaagtgtg gcatcctcct tatcgtgctc ctgacacacc tgcttgtgtc      600
agcccagacc ttgataagtt catattatgg tataaacctc gcgtcagcgt ttataatact      660
ggtgcttatg ggcacctggg cattgttagc tgcaggaggc agttgccgaa gcctgaaact      720
gtgcctgcta tgccaagata agaacttcct tctttagaac cagcgatcca gatatcctca      780
gggcaccagc acgtcccaaa cagcagacta tatctttagc ggaagcacga ctgtgccatt      840
ttctgataat cccttcttct ggtggaattg agaaagaaat aatactatgc acatatgcgt      900
gccaaaaaaa aaaaaaata  aaaaa                                            925

<210> SEQ ID NO 32
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 32
gatgactgct gccgtgttct tcggctgggc cttcatagcc ttcggtcctg cgctcgccct       60
ttaggtcttc acaatcgcca ctgagccgtt ccgtatcatg ttcctcatag ccggagcttt      120
cttctgcttg gtgtcgctac tgatatcgtc ccttgttggg ttcatggcaa gggtcattat      180
```

```
agacaacaat gatggaccca cacagaagta tctgctaatc tttggtgcgt ttgtctctgt    240
ctagatccaa gaaatgttcc gttttgcata ctataaactg ttaaaaaaag ccagtgatgg    300
tttgaacagt ataaagccag gtgaaacagc accttctatg cgcctgctgg cgtatgtttc    360
aggcttgggt tttggaatca tgagtggggt attttcattt gtgaataccc tatccgactc    420
cttggggcca ggaacagtgg gtattcatgg cgattctccg caattcttac tttattctgc    480
tttcatcacg ctggtgatta tcttactgca tgttttctgg ggcattgtat tgtttgatgg    540
atgtgagaat aaaaagtgcg gcatcctgct tatcgtactc ctgactcacc tgctcgtgtc    600
agcgcagacc ttaataagtt cttattatgg cataaacctg gcgtcagcat ttataattct    660
ggtgctcatg ggcacgtggg cattattagc tgctggaggc agctgccgaa ggctgaaact    720
atgcctgctt tgccaagaca agaacttgct tctttaaaac cagcgttcca gatacccctca    780 ggggaccagc acatcccaaa ctgcagacta catctttagg ggaagcacaa ctgtgccttt    840
ttctgacaat cccttgttct ggtgaaattg agatagaaat aacactatgc agatatgcgt    900
accaaaaaat aaaaaaaaca aaaaa                                           925

<210> SEQ ID NO 33
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 33
gatgactgcc gccgtgttgt tcggctgagc cttcattgcc ttcggccctg cgctggccct     60
ttaagtcttc actatcgcca ccgagccgtt gcgtatcata ttcctcattg ccggagcctt    120
cttctggttg gtgtcactac tgatttcgtc cctcgtttgg ttgatggcaa gagtcattat    180
tgacaacaac gatggaccga cacagaaata tctgcttatc tttggcgcgt ttgtgtctgt    240
ctaaatccaa gatatgttcc gctttgcata gtataaacta ttaaaaaatg ccagtgacgg    300
tttgaagagt ataaaaccag gtgatacagc accctctatg cggctgctgg catatgtttc    360
tggcttgggc tttggaatga tgagtggagt attttctttt gtgaacaccc tatcggactc    420
cttagggcca ggtacagtgg gcattcatgg ggattctcca caattctttc tttattccgc    480
tttcatgacg ctggtaatta tctttctgca tgtcttctgg gggattgtat tatttgatgg    540
ttgtgagaac aaaaagtggg gcatcctact tatcgttctc ctgacccacc tgctggtgtc    600
agcacagacc tttataagtt cctattatgg gataaaccta gcgtcagctt ttataatcct    660
ggtgctgatg ggcacatggg catttttagc tgccggaggc aggtgccgaa gactgaaact    720
ttgcctgctc tgccaagaga agaacttact tctttataac cagcgctcca gatagcctca    780
gggaaccagc acttcccaaa ccgcagacta gatctttaga ggaagcacta ctgtgccctt    840
ttctgagaat cccttattct ggtgtaattg agacagaaat aagactatgc aaatatgcgt    900
tccaaaaaac aaaaaaaga aaaa                                             925

<210> SEQ ID NO 34
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence
```

-continued

```
<400> SEQUENCE: 34
gatgactgcg gccgtgttat tcggctgtgc cttcatcgcc ttcgggcctg cgctagccct        60
ttatgtcttc accatcgcca cggagccgtt acgtatcatt ttcctcatcg ccggagcgtt       120
cttctgattg gtgtctctac tgatctcgtc cctggtttgg ttaatggcaa gtgtcattat       180
cgacaacaag gatggaccaa cacagaatta tctgctcatc tttggggcgt ttgtatctgt       240
ctatatccaa gacatgttcc ggtttgcata atataaactt ttaaaaaacg ccagtgaggg       300
tttgaaaagt ataaatccag gtgacacagc accgtctatg cgactgctgg cttatgtttc       360
cggcttgggg tttggaataa tgagtggtgt attttccttt gtgaagaccc tatcagactc       420
ctttgggcca ggcacagtgg ggattcatgg agattctcct caattcttcc tttattcggc       480
tttcataacg ctggttatta tcttcctgca tgtgttctgg ggaattgtat tttttgatgg       540
ctgtgagaag aaaaagtgag gcatccttct tatcgtcctc ctgacgcacc tgctagtgtc       600
agctcagacc ttcataagtt cgtattatgg aataaacctt gcgtcagcct ttataatgct       660
ggtgctaatg ggcacttggg cattcttagc tgcgggaggc agatgccgaa gtctgaaact       720
ctgcctgctg tgccaagaaa agaactttct tctttacaac cagcggtcca gataacctca       780
gggtaccagc acctcccaaa cggcagacta atctttagt ggaagcacca ctgtgccgtt       840
ttctgaaaat ccctttttct ggtgcaattg agagagaaat aaaactatgc atatatgcgt       900
cccaaaaaag aaaaaaaaaa aaaaa                                            925

<210> SEQ ID NO 35
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 35
gatgactgcg gcagtgttct ttggctgcgc cttcattgcg ttcgggccag cgctcgctct        60
ttatgtcttc accatggcca ccgaaccgtt gcgtatcatc ttcctcatcg cgggagcttt       120
attctggttt gtgtctctcc tgatttcgtc ccttgtatgg ttcattgcaa gagtcattat       180
tgagaacaaa gaaggaccaa ctcagaaata cctgctgatg tttggagcat ttgtctctgt       240
ctatatccaa gaaatgttcc gattagcata ttataaactc ttcaaaaaag cgagtgaagg       300
attgaagagt ataaaccccg gtgagacggc accctcaatg cgacttctgg cctacgtttc       360
tgggttgggc ttaggaatca ttagtggagt cttttccttg gtgaatacac tatctgattc       420
cttgggccca ggcacggtgg gcatacatgg agattctcct cacttcttcc tgtattcagc       480
attcatgact ctggtcatca tcttgctgca tgtattatgg ggcattgtat tttcgatgg       540 ctgggagaag aaaagtggg gtatcctcct catcgttctg ctgacccaac tgctggtttc       600
agcccacacc ttcatgagtt cttaatatgg aattaacctg gcctcagcat tgataatcct       660
agtgctcatt ggcacctgcg cattcttggc tgcgggaggc agctgtcgaa gcctcaaact       720
ctggctgctc tgacaagaca ataactttct cctttacaag cagcgctcaa gataacctca       780
gggaaccagc acttcgcaaa ccgcagacta catttttaga ggcagcacaa cggtgccttt       840
atctgaaaat ccctttttct ggtggaagtg agaaagaaat aaaactatgc agatctgcgt       900
tccgaaaaaa aaaaaaaaaa ataaa                                            925

<210> SEQ ID NO 36
```

```
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 36
gatgactgcg gctgtgttct tcggctgcgc gttcattgca ttcgggcctg cgctcgccct      60
ttatgtgttc accatagcca ccgatccgtt gcgcatcatc ttgctcatcg caggagcttt     120
tttctggttc gtgtctctgc tgatttcatc ccttgtttgg ttcatcgcaa gagtgattat     180
tgaaaacaaa gatggaccaa cccagaaata gctgctgata tttggagctt ttgtctccgt     240
ctatatgcaa gaaatattcc gatttgcata ttacaaactc ttgaaaaaag caagtgaagg     300
tttgaagagc ataaacccgg gtgagacagc accctctatg cgactcctgg cctaggtttc     360
tggattgggc tttggaatca tcagtggagt gttttcctta gtgaatactc tatctgactc     420
cttggggcca ggcacagtgg gcattcatgg agactctcct cagttcttcc tatattcagc     480
tttcatgacc ctggtcatga tcttgctaca tgtattttgg ggcatcgtat ttttggatgg     540
ctgagagaag aataagtggg gcatcctcct gatcgttcta ctgacccatc tgctggtctc     600
agcccagacc ttcataagtt cttattatgg aatcaacctg gcgtcagcat taataatcct     660
tgtgctcatc ggcacctggg cattcttagc tgcgggtggc agctgccgaa gcctgaaact     720
ctgactgctc tgtcaagaca caactttct gctttacaaa cagcgctcta gataaccccca     780 gggaacgagc acttcacaaa ccgctgacta catctttaga gggagcacaa cagtgccttt     840
ttctgaaaac ccctttttgt ggtggaaatg agaaagtaat aaaaccatgc agatgtgcgt     900
tccaaaaaaa aataaaaaaa acaaa                                           925

<210> SEQ ID NO 37
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 37
gatgactgcg gccgtgttct tgggctgcgc attcattgct ttcgggcccg cgctcgcgct      60
ttatgtattc accattgcca ccgacccgtt gcggatcatc ttactcatcg ctggagcttt     120
cttctggttg gtgtctctac tgatttcttc ccttgtctgg ttcatggcaa gagtaattat     180
tgataacaaa gacggaccaa cgcagaaata actgctgatt tttggagcct ttgtctcggt     240
ctatatacaa gaattttcc gattcgcata ttagaaactc ttaaaaaaag ctagtgaagg      300
cttgaagagg ataaacccag gtgagactgc accctccatg cgactgctgg cctaagtttc     360
tggtttgggc ttcggaatca tgagtggagt attttccttt gtgaatacc tatctgagtc      420 cttgggacca ggcactgtgg gcatccatgg agagtctcct caattcttcc tttattcagc     480
cttcatgacg ctggtcataa tcttgcttca tgtattctgg ggcatggtat ttttagatgg     540
ctgtgagaag aacaagtggg ggatcctcct aatcgttctt ctgacccacc tgctggtgtc     600
agcccaaacc ttcattagtt cttactatgg aatgaacctg gcatcagcat ttataatcct     660
cgtgctcatg ggcacctgag cattctttgc tgcgggcggc agctggcgaa gcctaaaact     720
ctgtctgctc tgccaagaca agaactttct acttacaat cagcgctcca gataaccgca      780
gggaacaagc acttctcaaa ccgccgacta catgtttaga ggaagcacaa ctgtgccttt     840
```

-continued

```
ctctgaaaag ccctttttat ggtggaattg agaaagcaat aaaacgatgc agatatgcgt      900
tcctaaaaaa aacaaaaaaa agaaa                                            925
```

<210> SEQ ID NO 38
<211> LENGTH: 925
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 38

```
gatgactgcg gcggtgttct taggctgcgc tttcattgcc ttcgggccgg cgctcgcact       60
ttatgttttc accatcgcca ccgagccgtt gcgaatcatc tttctcatcg ccggagcttt      120
gttctggtta gtgtctcttc tgatttcctc ccttgtgtgg ttcatagcaa gagttattat     180
tgacaacaaa gagggaccaa cacagaaata tctgctgatc tttggagcgt ttgtctcagt     240
ctatattcaa gaaatcttcc gattggcata ttaaaaactc tttaaaaaag ccagtgaagg     300
gttgaagaga ataaaccctg gtgagaccgc accctcgatg cgactactgg cctatgtttc     360
tggcttgggc ttgggaatca taagtggagt tttttccttc gtgaatacgc tatctgaatc     420
cttgggtcca ggcaccgtgg gcatgcatgg agaatctcct catttcttcc tctattcagc     480
gttcatgaca ctggtcatta tcttgctcca tgtattgtgg ggcatagtat tttttgatgg     540
ctgcgagaag aagaagtggg gaatcctcct tatcgttctc ctgacccagc tgctggtatc     600
agcccatacc ttcatcagtt cttagtatgg aataaacctg gcttcagcat tcataatcct     660
ggtgctcata ggcacctgtg cattcttcgc tgcgggggc agctgacgaa gccttaaact     720
ctgcctgctc tggcaagaca aaactttct tctttacaac cagcgctcga gataaccaca      780
gggaactagc acttcccaaa ccgcggacta catatttaga ggtagcacaa ccgtgccttt     840
gtctgaaaaa ccctttttt ggtggaactg agaaaggaat aaaacaatgc agatttgcgt     900
tcccaaaaaa aagaaaaaaa aaaaa                                            925
```

PRESENILIN ENHANCERS ASSAYS

FIELD OF THE INVENTION

The field of this invention is proteins which modulate presenilin function.

BACKGROUND

Azheimer's disease is a degenerative disorder of the central nervous system which causes memory impairment and cognitive loss during mid to late life. The disease is characterized by two primary pathological features, extracellular amyloid plaques in the brain, and intra-neuronal neurofibrillary tangles. These lesions inhibit neuronal and glial cell function, and lead to synaptic loss and dementia. Both early and late onset forms of the disease have been shown to have genetic components, and four genes have been definitively associated with increased risk for AD: APP, PS1, PS2 and ApoE. These genes are functionally linked by their roles in the production, transport, and/or elimination of, amyloid-β(Aβ), the primary constituent of Alzheimer's amyloid plaques (reviewed in Selkoe, D. 1999, Nature 399 supp: A23).

Alzheimer's amyloid plaques are comprised largely of the 40–42 amino acid peptide Aβ (Glenner, G. G., and Wong, C. W., 1984 Biochem. Biophys. Res. Commun. 122:1131). Aβ is derived by proteolytic cleavage from the b-Amyloid Precursor Protein, or βAPP (Kang J. et al. 1987, Nature 325:733). Three secretase activities cleave APP to generate the Aβ peptide or a shorter, alternative cleavage product called p3. β-secretase generates the N-terminus of Aβ, while α-secretase cleaves internal to Aβ sequences to generate the N-terminus of p3. γ-secretase cleaves the C-terminal β and α secretase products of APP to generate the heterogeneous C-terminal ends of Aβ and p3. APP mutations found in familial Alzheimer's disease (FAD) pedigrees are clustered around the three secretase cleavage sites (Goate, A., et al. 1991, Nature 349:704; Murrell, J., et al. 1991, Science 254: 97; Chartier-Harlin et al. 1991, Nature 353: 844; Mullan, M. et al. 1992, Nature Genet. 1: 345; Levy, E. et al., 1990, Science 248: 1124; Hendriks, L. et al. 1992, Nature Genet. 1:218) and they each increases total Aβ (Aβ42+Aβ40) or increases the Aβ 42/40 ratio. Since Aβ42 precipitates more readily in vitro and is the primary component of early forms of amyloid deposits called diffuse plaques, it has been postulated that increased systemic Aβ42 could lead to earlier formation of plaque, and earlier onset of AD.

Family studies identified two other genes, presenilin-1 (PS1) and presenilin-2 (PS2), associated with dominantly inherited, early onset AD, (Sherrington, R. et al. 1995, Nature 375: 754; Levy-Lahad, E. et al. 1995, Science 269: 973; Rogaev., E. I. et al. 1995, Nature 376: 775). These proteins are similar to each other in sequence and encode polytopic membrane proteins with 8 transmembrane segments. Studies in FAD human cell lines, in transfected cells, and in transgenic mice have demonstrated that the PS FAD mutations cause a change in the processing pattern of APP, resulting in an increased ratio of Aβ 42/40 (Scheuner, D. et al. 1996, Nat. Med. 2: 864; Citron, M. et al. 1997, Nat. Med. 3:67; Borchelt, D. et al. 1996, Neuron 17: 1005; Duff, K. et al. 1996, Nature 383: 710; Tomita, T. et al. 1997, PNAS 94:2025). Studies on PS1 knockout mice demonstrated that loss of PS1 function leads to reduction in Aβ production due to a reduction of γ-secretase activity (De Strooper, B. et al. 1998, Nature 391: 387). Presenilin function is thus implicated in the activity of γ-secretase in two ways: missense mutations alter g-secretase cleavage specificity, while loss of presenilin activity leads to loss of γ-secretase activity.

Inhibition of presenilin activity decreases Aβ production and is thus a potentially useful therapeutic approach to Alzheimer's disease. However, despite the functional link to γ-secretase activity and the generation of Aβ, the biochemical nature of PS activity is poorly understood. Various functions have been proposed, including action in the ER and/or Golgi complex as a chaperone for APP, Notch, and/or γ-secretase (Thinakaran, G. et al. 1998, Neurobiol. Dis. 4: 438), activity as a novel aspartyl protease, i.e. as g-secretase itself (Wolfe, M. S. et al. 1999, Nature 398: 513), and potential roles in the response to oxidative stress and apoptosis (Wolozin, B. et al. 1996, Science 274:1710; vito, P. et al. 1997, J. Biol. Chem 272: 28315; Guo, Q., et al. 1997, J. Neurosci. 17: 4212). The absence of a clear functional assay increases the difficulty of designing useful small molecule therapeutics targeted at presenilin. An alternative strategy to targeting presenilin is to discover additional proteins which act together with presenilins in the pathway of γ-secretase and Aβ production and which might be more amenable to drug development. One useful method for the discovery of such novel targets is to perform genetic screens in model organisms such as Drosophila and C. elegans for genes that interact with presenilins.

Invertebrate orthologues of the PS genes have been identified by both sequence searches and genetic screens. The C. elegans genome contains three presenilin genes, sel-12 (suppressor and/or enhancer of lin-12; Levitan, D. et al. 1995, Nature 377:351), hop-1 (homolog of presenilin; Li, X. et al, 1997, PNAS 94:12204) and spe-4 (spermatogenesis defective; L'Hernault et al., 1992, J. Cell Biol. 119:55). sel-12, hop-1 and spe-4 have 48, 35 and 23% sequence similarity, respectively, to PS1 and 2. sel-12 and hop-1 have overlapping functions in several tissues (see below), while spe-4 appears to perform an independent function in the male germ line. Rescue experiments using transgenes have shown that human PS1 and PS2 can rescue phenotypes caused by loss of sel-12, demonstrating that presenilin function has been conserved from nematodes to mammals (Levitan, D. et al. 1996, Nature 377:351; Baumeister, R. et al. 1997, Genes Function 1: 149).

Sel-12 was identified genetically as a suppressor of an activated allele of the Notch gene lin-12. This discovery established a functional link between presenilin activity and activity of the Notch signaling pathway. In vivo experiments in mice (Herreman, A. et al. 1999, PNAS 96:11872), Drosophila (Struhl, G. et al. 1999, Nature 398: 522; Ye, Y. et al. 1999 Nature 398:525) and C. elegans (Li, X. et al, 1997, PNAS 94:12204; Westlund, B. et al. 1999, PNAS 96:2497) have demonstrated that the phenotype of complete loss of presenilin activity corresponds very well with the complete elimination of Notch signaling in the organism, suggesting that presenilins are absolutely required for Notch signaling activity. Notch receptors are single pass transmembrane proteins present at the cell surface that mediate cell—cell signaling events critical to the differentiation of many embryonic and adult tissues in invertebrates and vertebrates. Signaling involves ligand-dependent cleavage of Notch at the inner face of the transmembrane segment, and subsequent nuclear translocation of the C-terminal domain. Analysis of Notch processing in cell culture and in vivo has further demonstrated that presenilins are required for the ligand dependent cleavage event that releases the Notch intracellular domain from the transmembrane domain (Struhl, G. et al. 1999, Nature 398: 522; De Strooper, B. et al. 1999 Nature 398: 518). The parallel requirement for presenilin in both the Notch and APP cleavages suggests that the Notch signaling pathway could be a useful surrogate assay in place of Ab production in screens for presenilin pathway genes.

Mutations in the *C. elegans* presenilins sel-12 and hop-1 result in phenotypes associated with defective signaling by the *C. elegans* Notch receptors lin-12 and glp-1. Loss of hop-1 alone results in no obvious phenotypes. Loss of sel-12 results in a strong egg-laying defective phenotype and vulval defects reminiscent of lin-12 mutations. Loss of both sel-12 and hop-1 produces more severe Notch phenotypes that seen in sel-12 alone. The specific phenotypes observed in the sel-12; hop-1 double mutants depends on whether these worms inherit maternal wild type presenilin activity. When maternally provided sel-12+ activity is present, the double mutant displays a novel egg-laying defective phenotype and all progeny arrest during embryogenesis with glp-1-like developmental defects. In the absence of maternal sel-12+ activity the double mutant exhibits a stonger phenotype of sterility with germline proliferation defects characteristic of glp-1 mutants. Together, this set of properties indicates that sel-12 and hop-1 are partially redundant and act coordinately to promote signaling by the two *C. elegans* Notch receptors.

The partial redundancy between sel-12 and hop-1 activities made it possible to look for enhancers of sel-12 loss of function alleles that would produce a phenotype equivalent to the sel-12; hop-1 double mutant. This enhancer screen identified two new genes which were named pen-1 and 2 (pen=presenilin enhancer) and which are required for presenilin function. Based on the phenotypes of the pen genes, we have identified a third presenilin enhancer gene, aph-2. The pen-1, pen-2 and aph-2 gene sequences identify orthologous genes in humans and other animals, including pen-1B. These genes and the processes they regulate are targets for the development of therapeutics for the treatment of Alzheimer's disease.

RELEVANT ART

Sequences related to a human pen-1 are found, inter alia, in WO9855508, WO9855508, WO9906554 and in Unigene CGI-78 (GI#6911522 and GI#4929623)

Sequences related to a human pen-2 are found, inter alia, in AD000671 (genomic) and GI#3601371 (cDNA).

Sequences related to a human Aph-2 are found inter alia, in WO 9845435, WO 9845436, WO 9300353 and (KIAA0253, DNA GI1665772, protein GI 1665773).

Numerous ESTs were found in public databases containing pieces of the natural human pen-1B sequence disclosed herein, including ns43g08.s1 (GI# 2874520, not annotated) and ESTs of Unigen contig Hs.42954 (53% similar to pen-1 (CGI-78)), including: AI538204 (IMAGE:2189986); AA808355 (IMAGE:1334417); N21153 (IMAGE:264868); AI204164 (IMAGE:1734840); AI001990 (IMAGE:1619191); AA578718 (IMAGE:953241); AA887975 (IMAGE:1160119); AI004282 (IMAGE:1626004); AI188040 (IMAGE:1738954); AI192033 (IMAGE:1738659); AI005113 (IMAGE:1626277); AW118908 (IMAGE:2605631); AI760754 (IMAGE:2398349); AA805770 (IMAGE:1186430); AA805757 (IMAGE:1186406); AW182071 (IMAGE:2662428); AA805773 (IMAGE:1186436); AI301191 (IMAGE:1897253); AA976455 (IMAGE:1589895); and N31710 (IMAGE:271292).

SUMMARY OF THE INVENTION

The invention provides methods, compositions and systems relating to presenilin enhancer proteins (pens), including methods for modulating (e.g. enhancing or inhibiting) and detecting presenilin-pen interactions. In a particular embodiment, the method provides for specifically detecting a stress that alters a functional interaction of a presenilin enhancer (pen) with upstream or downstream Notch or APP processing by: (i) introducing a predetermined stress into a system which provides a functional interaction of a pen with Notch or APP processing, whereby the system provides a stress-biased interaction of the pen with Notch or APP processing, wherein the absence of the stress, the system provides unbiased interaction of the pen with Notch or APP processing; and (ii) detecting the stress-biased interaction of the pen with Notch or APP processing, wherein a difference between the stress-biased and unbiased interactions indicates that the stress alters the interaction of the pen with Notch or APP processing.

The system may be a viable cell expressing the pen wherein the pen expression is determined to be non-natural or pathogenic, or an in vitro, cell-free mixture comprising a determined amount of the pen. A wide variety of embodiments are encompassed; for example, wherein the system is the viable cell, in situ or in vitro, and the stress is a pharmacologically active agent or a deficiency in functional expression of the pen, such as by virtue of genomic disruption of otherwise endogenous alleles encoding the pen or coexpression of a polynucleotide comprising a sequence antisense of an endogenous allele encoding the pen. Alternatively, the system may be the in vitro, cell-free mixture and the stress is a pharmacologically active agent. The stress-biased interaction of the pen with Notch or APP processing may be detected by any convenient means or marker, such as detecting an indication of Alzheimer's disease, a transcriptional reporter of notch, generation of a downstream product such as Aβ or a structural alteration in the pen, such as with a specific antibody.

The invention provides a variety of other methods and compositions relating to pen polypeptides having pen-specific structure and activity, related polynucleotides and modulators of pen function. The pen polypeptides may be recombinantly produced from transformed host cells from the subject pen polypeptide encoding nucleic acids or purified from natural sources such as mammalian cells. The invention provides isolated pen hybridization probes and primers capable of specifically hybridizing with natural pen genes, pen-specific binding agents such as specific antibodies, agonists and antagonists, and methods of making and using the subject compositions in diagnosis (e.g. genetic hybridization screens for pen transcripts), therapy (e.g. pen inhibitors to modulate Aβ production) and in the biopharmaceutical industry (e.g. as immunogens, reagents for isolating natural pen genes and transcripts, reagents for screening chemical libraries for lead pharmacological agents, etc.). In a particular aspect, the pen methods and compositions relate to pen-1B polypeptides.

DETAILED DESCRIPTION OF THE INVENTION

The invention provides methods, compositions and systems relating to presenilin enhancer proteins (pens), including methods for modulating (e.g. enhancing or inhibiting) and/or detecting an interaction between a pen and Notch or APP processing. In a particular embodiment, the method provides for specifically detecting a stress that alters a functional interaction of a presenilin enhancer (pen) with Notch or APP processing.

The pen is independently selected from a pen-1, pen-1B, pen-2 and Aph-2 polypeptide. These names are used generically to refer to polypeptides which comprise a disclosed parental sequence, comprise specified fragments thereof, or have sequence similarity to a disclosed parental sequence, wherein the sequence similarity is at least 40%, preferably at least 60%, more preferably at least 80%, more preferably at least 90%, more preferably at least 95%, most preferably 100%, and specifically bind a specifically disclosed presenilin or corresponding parental sequence pen-specific antibody, as measured in one or more of the disclosed interaction assays. The polypeptides comprise, and the similarity or identity extends over at least 10, preferably at least 15, more preferably at least 25, more preferably at least 35, more preferably at least 50 contiguous residues and most preferably over the entire polypeptide and/or parental pen sequence.

TABLE 1

Parental pen Polypeptides

| Parental pen | Natural Source | SEQ ID NO | % identity to human parental pen by BLAST |
|---|---|---|---|
| pen-1 | C. elegans | (SEQ ID NO:1) | 28.7 |
| | D. melanogaster | (SEQ ID NO:2) | 45.4 |
| | H. Virescens | (SEQ ID NO:3) | 50 |
| | mouse | (SEQ ID NO:4) | 92.8 |
| | human | (SEQ ID NO:5) | 100 |
| pen-1B | human | (SEQ ID NO:6) | 51 (identity to human parental pen-1) |
| pen-2 | C. elegans | (SEQ ID NO:7) | 42.6 |
| | D. melanogaster | (SEQ ID NO:8) | 60.4 |
| | rat | (SEQ ID NO:9) | 96 |
| | mouse | (SEQ ID NO:10) | 96 |
| | cow | (SEQ ID NO:11) | 95 |
| | human | (SEQ ID NO:12) | 100 |
| Aph-2 | C. elegans | (SEQ ID NO:13) | 18.9 |
| | D. melanogaster | (SEQ ID NO:14) | 29.9 |
| | human | (SEQ ID NO:15) | 100 |

For disclosed polymeric genuses, "percent (%) sequence identity over a specified window size W" with respect to parental sequences is defined as the percentage of residues in any window of W residues in the candidate sequence that are identical with the residues in the parent sequence, after aligning the sequences and introducing gaps, if necessary, to achieve the maximum percent sequence identity. The % identity values are generated by WU-BLAST-2.0 a19 obtained from Altschul et al., J. Mol. Biol., 215: 403–410 (1990); http://blast.wustl.edu/blast/README.html. WU-BLAST-2.0a19 which uses several search parameters, all of which are set to the default values. The HSP S and HSP S2 parameters are dynamic values and are established by the program itself depending upon the composition of the particular sequence and composition of the particular database against which the sequence of interest is being searched; however, the values may be adjusted to increase sensitivity. Hence, a % sequence identity value is determined by the number of matching identical residues divided by the window size W for which the percent identity is reported. Exemplary species are readily generated by mutating the corresponding parental sequences and confirming presenilin or antibody binding. For example, pen-1B polypeptides defined by SEQ ID NOS:16–25 exemplify an active (demonstrating presenilin binding) 90% genus around parental sequence SEQ ID NO:6. In particular embodiments, the pen is a natural pen, such as human, mouse, D. melanogaster, H. virescens or C. elegans pen-1; human, rat, mouse, cow, D. melanogaster or C. elegans pen-2; human pen-1B, and human, D. melanogaster or C. elegans Aph-2. In a particular aspect, the pen is a naturally-occurring pen identifiable in a sel-12Δ (Δ means deletion allele) homozygous C. elegans genetic mutation enhancer screen.

The interaction between the pen and Notch or APP processing may be detected in any convenient manner that specifically assays the pen influence on the processing pathway. The assay may be constructed to monitor a downstream perturbation in product generation (e.g. AΔ or Notch intracellular domain production), an intermediate pathway step (a number of intermediate Notch and APP processing pathway steps and intermediate component interactions are well documented in the art), or initiating pen-presenilin or pen-γ-secretase binding.

A wide variety of systems may be used in the methods. Detailed below are animal systems stressed with mutant pen genes to provide sensitized Notch and/or APP processing pathways, which systems are used to characterize additional interacting proteins. In particular embodiments, the system comprises a cell or animal expressing both the pen and a binding target such as a presenilin or γ-secretase, an in vitro, cell-free mixture comprising a determined amount of the pen and a binding target; applications of such cells and mixtures include two-hybrid, biochemical pull-down, immunoprecipitation, fluorescent polarization and solid phase binding assays. In accordance with the diversity of applicable systems, a wide variety of stresses may be assayed or evaluated, including chemical agents, such as candidate drugs, toxins, contaminants, etc.; radiation such as ultraviolet rays and x-rays; infection such as viral or bacterial infection including cellular transformation; genetic mutations etc.

The particular method used to detect the interaction of the pen polypeptide and the presenilin will depend on the nature of the assay, so long as the interaction is specifically detected. For example, as detailed below, modulation of pen mutant specific phenotypes provide readouts for genetic interaction assays. For in vitro assays, depending on if and how the pen polypeptide and/or target are labeled, the interaction readout may be measured by changes in fluorescence, optical density, gel shifts, radiation, etc. In a particular embodiment, the system provides a downstream APP processing readout.

In a particular embodiment, the methods involve specifically detecting a stress that alters a physical interaction of a subject pen polypeptide with APP and/or Notch processing. In one aspect, this embodiment comprises the steps of (a) introducing a predetermined stress into a system which provides a physical interaction of a pen with a binding target, whereby the system provides a stress-biased interaction of the pen and the target, wherein the absence of the stress, the system provides an unbiased interaction of the pen polypeptide and the target; and (b) detecting the stress-biased interaction of the pen polypeptide and the target, wherein a difference between the stress-biased and unbiased interactions indicates that the stress alters the interaction of the pen polypeptide and the target, wherein preferred targets include γ-secretases, presenilins, notch and/or APP substrates, and/or combinations and complexes thereof.

In the latter embodiment, the presenilin is selected from a presenilin-1 (PS-1) and presenilin-2 (PS-2). These names are used generically to refer to polypeptides which comprise a disclosed parental sequence, comprises specified fragments thereof, or have sequence similarity to the disclosed parental presenilin sequences, wherein the sequence similarity is at least 50%, more preferably at least 70%, more preferably at least 80%, more preferably at least 90%, more preferably at least 95% and most preferably 100%, wherein the presenilin is sufficient to provide a presenilin-specific, detectable functional interaction comparable to that provided by the corresponding parental sequence presenilin, as measured in one or more of the disclosed genetic or biochemical interaction assays. The presenilins comprise, and the similarity or identity extends over at least 10, preferably at least 15, more preferably at least 25, more preferably at least 35, more preferably at least 50 contiguous residues and most preferably over the entire presenilin or parental sequence. The parental presenilin is selected from a natural sequence presenilin 1 (such as human, mouse, chicken and xenopus sequences) and presenilin 2 (such as human, mouse and xenopus sequences), which are known in the art and accessible from public genetic depositories such as Genbank.

The compositions of the invention, useful in the subject methods, include the subject pen polypeptides and mixtures comprising predetermined amounts of a disclosed pen and presenilin polypeptides, particularly wherein one, preferably both of these components are isolated and mixtures consisting essentially of both components, i.e. wherein other components of the mixture (except for an assayed stress) do not significantly influence the interaction of these two components. Other aspects of the invention include nucleic acids encoding the disclosed pen polypeptides, antibodies which specifically bind them, and methods of use.

Subject polypeptides consisting of the disclosed parental sequences or fragments thereof are isolated, i.e. encompass pen polypeptides covalently joined to a non-natural or heterologous component, such as a non-natural amino acid or amino acid sequence or a natural amino acid or sequence other than that which the polypeptide is joined to in a natural protein, are preferably in solution, and preferably constitute at least about 0.5%, and more preferably at least about 5% by weight of the total polypeptide in a given sample and pure polypeptides constitute at least about 90%, and preferably at least about 99% by weight of the total polypeptide in a given sample, as are preferred subject polypeptides comprising other than parental sequence. The polypeptides may be covalently or noncovalently part of a larger complex, such as larger polypeptides and/or various conjugates, etc. The polypeptides may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The pen encompassing fragments comprise at least 10, preferably at least 15, more preferably at least 25, more preferably at least 35, most preferably at least 50 consecutive residues of a corresponding disclosed parental pen sequence. Pen polypeptides provide corresponding pen specific function, such as interacting with a component of a natural notch or APP processing pathway, especially presenilin binding or binding inhibitory activity as shown in one or more binding assays as described herein, and/or pen specific antibody binding or binding inhibitory activity, particularly as measured in a disclosed binding assay.

Pen-specific function may be determined by convenient in vitro, cell-based, or in vivo assays, e.g. binding assays. The term binding assay is used generically to encompass any assay, including in vitro, cell-cuture or animal-based assays (e.g. using gene therapy techniques or with transgenics), etc. where the molecular interaction of a pen polypeptide with a specific binding target is evaluated. The binding target may be a natural intracellular binding target such as a presenilin, a pen regulating protein or other regulator that directly modulates pen activity or its localization; or non-natural binding target such as a specific immune protein such as an antibody, or a pen specific agent such as those identified in screening assays such as described below. Pen-binding specificity may be assayed by APP processing (e.g. ability of the subject polypeptides to function as negative effectors in pen-expressing cells), by binding equilibrium constants (usually at least about $10^7 M^{-1}$, preferably at least about $10^8 M^{-1}$, more preferably at least about $10^9 M^{-1}$), by immunogenicity (e.g. ability to elicit pen specific antibody in a heterologous host such as a mouse, rat, goat or rabbit), etc.

In a particular embodiment, the subject polypeptides provide pen-specific antigens and/or immunogens, especially when coupled to carrier proteins. For example, the subject polypeptides are covalently coupled to keyhole limpet antigen (KLH) and the conjugate is emulsified in Freunds complete adjuvant. Laboratory rabbits are immunized according to conventional protocol and bled. The presence of pen-specific antibodies is assayed by solid phase immunosorbant assays using immobilized corresponding pen polypeptides, see, e.g. Table 2.

TABLE 2

Immunogenic pen-1B polypeptides eliciting pen-1B-specific rabbit polyclonal antibody: pen-1B polypeptide-KLH conjugates immunized per protocol described above.

| pen-1B Polypeptide Sequence | Immunogenicity |
|---|---|
| SEQ ID NO:6, res 1–14 | +++ |
| SEQ ID NO:6, res 6–15 | +++ |
| SEQ ID NO:6, res 10–20 | +++ |
| SEQ ID NO:6, res 25–46 | +++ |
| SEQ ID NO:6, res 62–71 | +++ |
| SEQ ID NO:6, res 67–76 | +++ |
| SEQ ID NO:6, res 72–95 | +++ |
| SEQ ID NO:6, res 115–126 | +++ |
| SEQ ID NO:6, res 130–140 | +++ |
| SEQ ID NO:6, res 139–151 | +++ |
| SEQ ID NO:6, res 166–182 | +++ |
| SEQ ID NO:6, res 184–198 | +++ |
| SEQ ID NO:6, res 214–232 | +++ |
| SEQ ID NO:6, res 246–257 | +++ |

The subject pen polypeptides also encompass minor deletion mutants, including N-, and/or C-terminal truncations, of the parental pen polypeptides. Such deletion mutants are readily screened for pen competitive or dominant negative activity. Exemplary active deletion mutants for pen-1B include polypeptides comprising an amino acid sequence selected from the group consisting of: SEQ ID NO:6, residues 1–254; SEQ ID NO:6, residues 4–255; SEQ ID NO:6, residues 9–257; and SEQ ID NO:6, residues 2–255.

The invention provides binding agents specific to the claimed pen-1B polypeptides, including natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with unoptimized utilization of a pathway involving pen, e.g. APP processing. Novel pen-specific binding agents include pen-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as in vitro, cell-based and animal-based binding assays described herein, or otherwise known to those of skill in the art, etc. Agents of particular interest modulate pen function, e.g. pen-dependent Notch or APP processing, and include dominant negative deletion mutants, etc. Accordingly, the invention also provides methods for modulating APP processing in a cell comprising the step of modulating pen activity, e.g. by contacting the cell with a modulator of a resident pen, a dominant negative pen deletion mutant, or pen polynucleotide (below).

In addition to direct synthesis, the subject polypeptides can also be expressed in cell and cell-free systems (e.g. Jermutus L, et al., Curr Opin Biotechnol. 1998 October; 9(5):534–48) from encoding polynucleotides, such as the corresponding parent polynucleotides or naturally-encoding polynucleotide isolated with degenerate oligonucleotide primers and probes generated from the subject polypeptide sequences ("GCG" software, Genetics Computer Group, Inc, Madison Wis.) or polynucleotides optimized for selected expression systems made by back-translating the subject polypeptides according to computer algorithms (e.g. Holler et al. (1993) Gene 136, 323–328; Martin et al. (1995) Gene 154, 150–166). Hence, the polypeptides may be synthesized, produced by recombinant technology, or purified from cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides polynucleotides encoding the disclosed polypeptides, and pen-gene specific polynucleotides, which polynucleotides may be joined to other components such as labels or other polynucleotide sequences (i.e. they may be part of larger sequences) and are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant polynucleotides comprising natural sequence contain such sequence at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bases, most preferably fewer than 100 bases, which is at a terminus or is immediately flanked by a sequence other than that which it is joined to on a natural chromosome. While the polynucleotides are usually RNA or DNA, it is often advantageous to use polynucleotides comprising other bases or nucleotide analogs to provide modified stability, etc. Futhermore, the terms polynucleotide and nucleic acid are used interchangeably to refer to any polymer of nucleotides, without restriction by length.

The invention also encompasses pen, particularly pen-1B gene specific polynucleotides. For example, the nucleotide sequence of a natural human transcript encoding a natural human pen-1B polypeptide is shown as SEQ ID NO:26. The term pen-1B gene specific polynucleotides is used generically to refer to polynucleotides comprising SEQ ID NO:26, comprising specified fragments of SEQ ID NO:26, or having sequence similarity to SEQ ID NO:26. Subject fragments of SEQ ID NO:26, which are useful, e.g. as. hybridization probes and replication/amplification primers, comprise at least 12, preferably at least 24, more preferably at least 48, more preferably at least 96 and most preferably at least 182 contiguous nucleotides of SEQ ID NO:26.

Pen gene specific polynucleotides effect specific hybridization to the corresponding parental sequence or complement thereof; for example, all pen-1B gene specific polynucleotides effect specific hybridization to SEQ ID NO:26 or its complement. Demonstrating specific hybridization generally requires stringent conditions, for example, hybridizing in a buffer comprising 30% formamide in 5×SSPE (0.18 M NaCl, 0.01 M NaPO$_4$, pH 7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Specifically hybridizing polynucleotides are readily identified in convenient gel-based assays; for example, polynucleotides comprising SEQ ID NOS:27–38 are shown to specifically hybridize with SEQ ID NO:26 under the foregoing preferred hybridization conditions.

TABLE 3

Exemplary pen-1B gene specific polynucleotides which hybridize with a strand of SEQ ID NO:26 under Conditions I and II.

| pen-1B gene specific polynucleotides | Specific Hybrids |
| --- | --- |
| SEQ ID NO:26, nucl 1–36 | + |
| SEQ ID NO:26, nucl 32–68 | + |
| SEQ ID NO:26, nucl 65–97 | + |
| SEQ ID NO:26, nucl 103–140 | + |
| SEQ ID NO:26, nucl 131–154 | + |
| SEQ ID NO:26, nucl 148–182 | + |
| SEQ ID NO:26, nucl 222–256 | + |
| SEQ ID NO:26, nucl 258–286 | + |
| SEQ ID NO:26, nucl 273–305 | + |
| SEQ ID NO:26, nucl 318–352 | + |
| SEQ ID NO:26, nucl 344–376 | + |
| SEQ ID NO:26, nucl 352–386 | + |
| SEQ ID NO:26, nucl 388–424 | + |
| SEQ ID NO:26, nucl 406–431 | + |
| SEQ ID NO:26, nucl 420–446 | + |
| SEQ ID NO:27 | + |
| SEQ ID NO:28 | + |
| SEQ ID NO:28 | + |
| SEQ ID NO:30 | + |
| SEQ ID NO:31 | + |
| SEQ ID NO:32 | + |
| SEQ ID NO:33 | + |
| SEQ ID NO:34 | + |
| SEQ ID NO:35 | + |
| SEQ ID NO:36 | + |
| SEQ ID NO:37 | + |
| SEQ ID NO:38 | + |

The subject nucleic acids find a wide variety of applications including use as translatable transcripts, hybridization probes, PCR primers, diagnostic nucleic acids, etc.; use in detecting the presence of other pen gene specific polynucleotides and gene transcripts and in detecting or amplifying nucleic acids encoding additional pen homologs and structural analogs. For example, pen-encoding polynucleotides may be used in pen-expression vectors, generally operably linked to a heterologous promoter, and/or incorporated into recombinant host cells, e.g. for expression and screening, transgenic animals, e.g. for functional studies such as the efficacy of candidate drugs for disease associated with pen-modulated cell function, etc. In diagnosis, pen hybridization probes find use in identifying wild-type and mutant pen alleles in clinical and laboratory samples. Mutant alleles are used to generate allele-specific probes for high-throughput clinical diagnoses, e.g. for pen mutations associated with Alzheimer's disease. In therapy, therapeutic pen polynucleotides are used to modulate cellular expression or intracellular concentration or availability of active pen.

For example, pen polynucleotides are used to modulate cellular expression or intracellular concentration or availability of active pen protein. Pen inhibitory nucleic acids are typically antisense: single-stranded sequences comprising complements of the disclosed natural pen transcript sequence. Antisense modulation of the expression of a given pen polypeptide may employ antisense nucleic acids operably linked to gene regulatory sequences. Cells are transfected with a vector comprising a pen gene specific polynucleotide sequence with a promoter sequence oriented such that transcription of the gene yields an antisense transcript capable of binding to endogenous pen encoding mRNA. Alternatively, single-stranded antisense polynucleotides that bind to genomic DNA or mRNA encoding pen polypeptide may be administered to the target cell, in or temporarily isolated from a host, at a concentration that results in a substantial reduction in expression of the targeted protein. An enhancement in pen expression is effected by introducing into the targeted cell type pen polynucleotides that increase the functional expression of the corresponding gene products. Such polynucleotides may be pen expression vectors, vectors that upregulate the functional expression of an endogenous allele, or replacement vectors for targeted modification of endogenous mutant or wild type alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of a pen modulatable cellular function and/or pen gene expression, including transcription. A wide variety of assays for transcriptional modulators or binding agents is provided including labeled in vitro ligand binding assays, immunoassays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

A wide variety of assays for binding agents, i.e. screens for compounds that modulate pen interaction with a natural pen binding target are also provided. These assays employ a mixture of components including a pen polypeptide, which may be part of a fusion product with another polypeptide, e.g. a peptide tag for detection or anchoring, etc. The assay mixtures comprise a natural intracellular pen binding target. In a particular embodiment, the binding target is presenilin, or portion thereof which provides binding affinity and avidity to the subject pen polypeptide conveniently measurable in the assay and preferably comparable to the intact presenilin. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc.

The resultant mixture is incubated under conditions whereby, but for the presence of the candidate pharmacological agent, the pen polypeptide specifically binds the cellular binding target, portion or analog with a reference binding affinity. The mixture components can be added in any order that provides for the requisite bindings, and incubations may be performed at any temperature which facilitates optimal binding. Incubation periods are likewise selected for optimal binding but also minimized to facilitate rapid, high-throughput screening.

After incubation, the agent-biased binding between the pen polypeptide and one or more binding targets is detected by any convenient way. A variety of methods may be used to detect the change depending on the nature of the product and other assay components, e.g. through optical or electron density, radiative emissions, nonradiative energy transfers, etc. or indirect detection with antibody conjugates, etc. A difference in the binding affinity of the pen-1B to the target in the absence of the agent as compared with the binding affinity in the presence of the agent indicates that the agent modulates the binding of the pen to the pen binding target. A difference, as used herein, is statistically significant and preferably represents at least a 50%, more preferably at least a 90% difference.

The following experimental section and examples are offered by way of illustration and not by way of limitation.

EXAMPLES, PROTOCOLS AND EXPERIMENTAL PROCEDURES

I. High-Throughput In Vitro Fluorescence Polarization Assay

Reagents:
  pen peptide (size minimized, rhodamine-labeled; final conc.=1–5 nM)
  PS polypeptide (final conc.=100–200 nM)
  Buffer: 10 mM HEPES, 10 mM NaCl, 6 mM magnesium chloride, pH 7.6

Protocol:
  1. Add 90 microliters of pen peptide/PS polypeptide mixture to each well of a 96-well microtiter plate.
  2. Add 10 microliters of test compound per well.
  3. Shake 5 min and within 5 minutes determine amount of fluorescence polarization by using a Fluorolite FPM-2 Fluorescence Polarization Microtiter System (Dynatech Laboratories, Inc).

II. Conformational Sensor—ELISA Format Assay

Buffer and Solution Preparation:
  1. 10× Assay Buffer:
     100 mL of 1M Hepes
     300 mL of 5M NaCl
     20 mL of 1M MgCl
     Add MQ H2O to 1 L 2. Master Mix of peptide/protein
    Protein: Glutathione-S-transferase/γ-secretase polypeptide fusion protein: final conc=100 nM
    pen peptide (size minimized, biotinylated; final conc.=1 uM)
    Add Assay Buffer and H2O to bring to final volume: final buffer conc=1×
3. Antibody Mix:
    anti-GST, rabbit (final conc.=1:10,000)
    anti-rabbit-HRP (final conc.=1:10,000)
    Add T-TBS to bring to final volume: final buffer conc=1×

Procedure:
1. Make 50 mL of Master Mix (see 2 above) of appropriate peptide/protein combinations (use 50 mL polypropylene tubes). Incubate for 1 hr at RT
2. Add 95 uL of Master Mix to each well of a 96-well plate**
    ** Reacti-Bind Streptavidin-Coated, White Polystyrene Plates (#15118B), which have been blocked by Super-Blocking Reagent from Pierce.
3. Transfer 5 uL of each test compound (stock=60 uM) to each well of the plate
4. Incubate plate for 1 hr at RT
5. While incubating, make rabbit anti-GST antibody and anti-rabbit-HRP Antibody Mix (see 3 above). Incubate on ice for 1 hr.
6. Wash plates 3× with H2O thoroughly
7. Add 100 uL of Antibody Mix into each well of the plate
8. Incubate for 1 hr at RT
9. Wash 3× with H2O
10. Dilute Supersignal substrate (mixed Luminol and peroxide) in 1:2H2O and then add 100 uL into each well
11. Shake 3–5 min. Read chemiluminescence.

III. High-Throughput In Vitro Binding Assay.

A. Reagents:
    Neutralite Avidin: 20 μg/ml in PBS.
    Blocking buffer: 5% BSA, 0.5% Tween 20 in PBS; 1 hour at room temperature.
    Assay Buffer: 100 mM KCl, 20 mM HEPES pH 7.6, 1 mM $MgCl_2$, 1% glycerol, 0.5% NP-40, 50 mM b-mercaptoethanol, 1 mg/ml BSA, cocktail of protease inhibitors.
    $^{33}$P pen peptide 10× stock: $10^{-8}$–$10^{-6}$ M "cold" pen peptide supplemented with 200,000–250,000 cpm of labeled pen peptide (Beckman counter). Place in the 4° C. microfridge during screening.
    Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$(Sigma # S-6508) in 10 ml of PBS.
    Binding Polypeptide: $10^{-7}10^{-5}$ M biotinylated PS polypeptide in PBS.

B. Preparation of Assay Plates:
    Coat with 120 μL of stock N-Avidin per well overnight at 4° C.
    Wash 2 times with 200 μl PBS.
    Block with 150 μl of blocking buffer.
    Wash 2 times with 200 μl PBS.

C. Assay:
    Add 40 μl assay buffer/well.
    Add 10 μl compound or extract.
    Add 10 μl $^{33}$P-pen peptide (20–25,000 cpm/0.1–10 pmoles/well=$10^{-9}$–$10^{-7}$ M final conc).
    Shake at 25° C. for 15 minutes.
    Incubate additional 45 minutes at 25° C.
    Add 40 μM biotinylated PS polypeptide (0.1–10 pmoles/ 40 ul in assay buffer)
    Incubate 1 hour at room temperature.
    Stop the reaction by washing 4 times with 200 μM PBS.
    Add 150 μM scintillation cocktail.
    Count in Topcount.

D. Controls for All Assays (Located on Each Plate):
    a. Non-specific binding
    b. Soluble (non-biotinylated PS polypeptide) at 80% inhibition.

IV. Identification of Presenilin Enhancer Genes: Natural Pen-1 and Pen-2.

The partial redundancy of sel-12 and hop-1 means that, for most tissues, a deletion of one or the other gene will result in only a partial loss of presenilin function. Hence, a knock-out mutation in one or the other gene provides a sensitized background for genetic screens designed to identify presenilin interacting genes. Using this reasoning, we designed several variations of genetic screens aimed at identifying genes that act in concert with presenilins. One variation (Screen A) is to mutagenize worms homozygous for a sel-12 deletion mutation (hereinafter referred to as sel-12Δ) and screen for enhancer mutations that, in combination with sel-12Δ, produce phenotypes equivalent to those of the sel-12Δ; hop-1Δdouble mutant. Such enhancer mutations identify both 1) components that interact uniquely with hop-1 presenilin and 2) components that interact with both hop-1 and sel-12 presenilins. As an internal control, Screen A is expected to yield loss-of-function hop-1 alleles since the screen targets the phenotypes seen in the sel-12Δ; hop-1 Δ double mutant. Another variation is to mutagenize a hop-1 single mutant and again screen for enhancement to the phenotypes associated with a complete presenilin.

In addition to the desired mutations that enhance presenilin defects, these screens identify mutations in known components of the glp-1 signaling pathway (e.g., glp-1/Notch receptor, lag-2/DSL ligand, lag-2/Su(H) family effector) since loss of these gene products results in glp-1 like sterility. An important distinction between presenilin enhancers and mutations in known glp-1 pathway genes is that former result in glp-1-like sterility only in a sel-12Δ background whereas the latter result in glp-1 sterility in both a wild-type genetic background (Austin, J. and Kimble, J., Cell (1987) 51:589–599; Lambie, E. and Kimble, J., Development 1991) 112:231–240) and a sel-12Δ background.

We performed Screen A on a large scale, screening approximately 128,000 haploid genomes after mutagenesis of a sel-12Δ homozygous strain with ethyl methane sulfonate. The screen resulted in the isolation of the expected types of mutants, including 27 putative glp-1 alleles, 3 mutations identified as likely lag-1 or lag-2 alleles based on map position, and 8 hop-1 mutations. As expected, the putative glp-1, lag-1, and lag-2 mutations result in glp-1-like sterility in both a wild type and a sel-12Δ genetic background; these mutations therefore cause sterility independently of the presence or absence sel-12+ function. By contrast, the 8 hop-1 mutations result in a penetrant glp-1-like sterile phenotype in the absence, but not the presence, of sel-12+ activity.

In addition to the preceding, we isolated 7 mutants that, based on mapping and complementation tests, identify two new presenilin-interacting genes. Four of these mutants identify the gene pen-1 located on chromosome I and other three identify the gene pen-2 located on chromosome III. Our subsequent work with these genes indicated: 1) that the pen-1 and pen-2 enhancers alleles are loss-of-function mutations; 2) that loss of pen-1+ or pen-2+ function, in combination with a loss of sel-12+ function, has the same phenotypic consequences as a complete loss of presenilin function; 3) that loss of pen-1+ and pen-2+ function in a sel-12+ background results in phenotypes indicative of a partial loss of presenilin/Notch pathway function; 4) that pen-1 and pen-2 interact genetically with both sel-12 and hop-1; 5) that the open reading frames for pen-1 and pen-2 encode unrelated integral membrane proteins; 6) that pen-1 and pen-2 related genes are conserved across phyla.

Pen-1 and pen-2 mutations enhance sel-12Δ to the lin-12/glp-1-like phenotypes associated with total presenilin loss. As double mutants with a sel-12Δ mutation, pen-1 alleles and pen-2 alleles each result in a set of phenotypes identical with those seen in sel-12Δ; hop-1Δ worms that receive no maternal sel-12+ activity. Specifically, each of these double mutants with sel-12Δ share 3 common abnormalities that are not seen in sel-12Δ or hop-1 Δ single mutants, or in pen-1 or pen-2 single mutants. First, all three sets of double mutants display indistinguishable glp-1-like sterile phenotypes characterized by germ cell proliferation defect similar to that described for glp-1 loss-of-function mutants (Austin and Kimble, 1987). Second, all three double mutants show a common cell fate specification defect(s) that indicates a loss of lin-12/Notch signaling. lin-12+ activity is required for the ventral uterine precursor versus anchor cell fate decision: lin-12(1f) mutants have 2 anchor cells rather than the normal complement of one because the cell that normally adopts the ventral uterine precursor fate instead becomes an anchor cell (Greenwald, I. et al., Cell (1983) 34:435–444). The sel-12Δ; pen-1 and sel-12Δ; pen-2 double mutants display this "2 anchor cell" phenotype just as does the sel-1 Δ2; hop-1Δ double mutant (Westlund; B et al., Proc. Natl. Acad. Sci. (1999) 96: 2497–2502). Third, sel-12Δ; pen-1 and sel-12Δ; pen-2 double mutants, like sel-12Δ; hop-1Δ, display an everted vulva phenotype that is reminiscent of vulva defects seen in lin-12(1f) mutants.

The above phenotypic comparisons demonstrate that a reduction in pen-1+ or pen-2+ activity, in combination with a loss of sel-12+ activity, results in a loss of presenilin pathway function comparable to the effects of eliminating the two redundant presenilins encoded by sel-12 and hop-1.

Single pen-1 and pen-2 mutations confer phenotypes associated with partial loss of presenilin function. As single mutants, pen-1 and pen-2 worms display two visible abnormalities. First, pen-1 and pen-2 homozygotes (produced from a pen-1/+ or pen-2/+ mother) both produce normal numbers of self-progeny embryos but these embryos are retained in the animal's uterus and never laid. pen-1 and pen-2 hermaphrodites are thus egg-laying defective (or Egl), a phenotype shared by the sel-12Δ single mutant.

Second, the embryos produced by homozygous pen-1 or pen-2 hermaphrodites never hatch but instead arrest in development with multiple abnormalities. The arrested embryos produced by pen-1 and pen-2 hermaphrodites show very similar abnormalities. Most strikingly, many of the arrested embryos make only a partial pharynx: the posterior pharnygeal lobe is present, but the anterior lobe is absent. Absence of anterior pharynx, called an Aph phenotype (for no anterior pharynx), was first described for certain weak alleles of glp-1. The GLP-1 receptor is required for a specific embryonic signaling event that induces formation of anterior pharynx (Mello, C. et al., Cell (1994) 77: 95–106; Moscovitz, I et al., Development (1994) 120:3325–3338; Hutter, H. and Schnabel, R., Development (1994) 120:2051–2064); absence of maternally provided glp-1+ activity can thus result in the Aph phenotype as well as other defects (Priess, J. et al., Cell (1987) 5:601–611). A connection of the Aph phenotype with reduced presenilin function comes from analysis of sel-12Δ; hop-1Δ hermaphrodites which receive maternal sel-12+ (which rescues the sterility seen in the absence of maternal sel-12+ function). In this situation, sel-12Δ; hop-1Δ hermaphrodites produce arrested embryos which display the Aph phenotype, as well addition to other glp-1 like embryonic defects (Westlund, B., supra). These properties of pen-1 and pen-2 indicate both genes act in concert with both sel-12 and hop-1 presenilins, since the loss of pen-1 or pen-2 causes phenotypes more severe than those cause by the sel-12 or hop-1 single mutant.

In addition to the Aph phenotype, embryos produced by homozygous pen-1 or pen-2 hermaphrodites display other abnormalities. The embryos usually arrest with little evidence of elongation and the embryonic hypodermis (layer of epidermal cells that lies under and secrets the cuticle) often fails to fully enclose other cell types. Similar phenotypes have been described for embryos produced by glp-1(ts) mutants.

In summary, pen-1 and pen-2 mutants share multiple phenotypes (Egl, Aph and defective embryonic elongation) that are indicative of cell signaling defects involving the Notch family receptors glp-1 and lin-12. In addition, in combination with sel-12Δ, pen-1 and pen-2 result in additional, stronger Notch pathway-related defects (glp-1-like sterility, 2 anchor cell phenotype; vulva eversion). The combined genetic and phenotypic evidence indicates that pen-1 and pen-2 are novel components that may assist presenilins in Notch receptor maturation and/or processing.

Pen-1 corresponds to the predicted *C. elegans* gene VF36H2L. 1. To clone pen-1, we genetically mapped pen-1(ep140) to increasingly smaller intervals, first using visible genetic markers and then using molecular markers [Tc1 transposon insertions and single nucleotide polymorphisms (SNPs)]. The final stage of SNP mapping of pen-1 narrowed its position to a 52 KB interval on chromosome I. This interval, as documented in the *C. elegans* database ACEDB (Eeckman, F. and Durbin, R. *C. elegans*: Modern Biological Analysis of an Organism (1995) pp. 583–599), contains a total of 7 predicted genes. One of these, VF36H2L.1, was identified as pen-1 on the basis of RNA-mediated interference (RNAi) data and mutation detection. For many *C. elegans* genes, RNAi disrupts both maternal and zygotic gene activity (Tabara, H. et al. Science (1998) 282:430–431). In case of pen-1, disruption of maternal activity after injection of dsRNA into adult hermaphrodites was evidenced by the production of developmentally arrested embryos with an Aph phenotype. As expected, this phenotype was observed after RNAi of both wild-type and sel-12Δ hermaphrodites. RNAi in either background also gave many viable escaper progeny that grew to adulthood. In the case of RNAi in a sel-12Δ background, a high proportion of these escapers displayed glp-1-like sterility, consistent with inhibition of zygotic pen-1 activity. Unexpectedly, RNAi of VF36H2L.1 in wild type also resulted in Glp sterile progeny, although at a much lower frequency than in with pen-1 RNAi in a sel-12Δ homozygotes. By contrast, glp-1-like sterility is never observed in pen-1 single mutants. This difference is most likely attributable to the property that RNAi typically disrupts both maternal and zygotic gene function, and can therefore result in more severe phenotypes than seen in zygotically lethal mutations.

By sequence analysis, we determined that the four pen-1 alleles isolated as sel-12 enhancers each contain single-nucleotide substitutions in the VF36H2L.1 open reading frame. Remarkably, these 4 independently-derived lesions are each nonsense mutations in the same codon, Trp191. Three alleles (ep140, ep168, and ep170) are third base UGG to UGA alterations, while the fourth (ep216) is a second base UAG to UGG change. That these lesions result in Aph and glp-1 like sterility phenotypes similar to RNAi of VF36H2L.1, indicates that they are reduction-of-function mutations.

Pen-1 encodes an evolutionarily conserved protein with multiple transmembrane domains. The pen-1 (VF36H2L.1, GI#2815036) open reading frame is split among 4 exons that, when spliced, encode a 308 amino-acid protein. We confirmed the predicted splice junctions of exons 2 and 3 by sequence analysis of partial cDNA product. Pen-1 shows homology with the predicted structures of various human, mouse, and Drosophila proteins, as described in detail below. Pen-1 is a predicted integral membrane protein that, as determined by the structure predicting programs PSORT2 and TopPred2, may contain up to 7 membrane-spanning domains.

Pen-2 corresponds to predicted C. elegans gene T28D6.9. We genetically mapped pen-2 to chromosome III between the cloned genes pha-1 and dpy-18. This interval spans approximately 240 KB of DNA and contains 31 predicted genes as documented in ACEDB ver. 9 (Eeckman, F. and Durbin, R., C. elegans: Modern Biological Analysis of an Organism (1995) pp. 583–599). pen-2 was identified as the predicted gene T28D6.9 on the basis of RNAi data and mutation detection. RNAi of most of the genes in the interval led to the identification of, T28D6.9, as the only candidate gene for which RNAi gave the expected maternal and zygotic pen-2 phenotypes. Wild type and sel-12Δ hermaphrodites injected with T28D6.9 produced a high proportion of developmentally-arrested embryos, many of which were Aph. In addition, RNAi of sel-12Δ (but not wild type) worms resulted in viable "escaper" progeny that displayed glp-1 like sterility. Mutation detection for the three pen-2 alleles isolated as sel-12 enhancers revealed that each contains a nonsense mutation in the T28D6.9 predicted open reading frame. Two lesions (ep219 and ep220) alter the Trp74 codon, changing it from UGG to UGA (ep219) or UAG (ep220), while the third lesion (ep221) changes Trp36 to a UGA stop codon. These nonsense alleles should strongly reduce or abolish gene function, indicating that enhancement of sel-12Δ results from a loss of wild-type pen-2+ activity.

Pen-2 encodes a predicted multi-pass membrane protein. The pen-2 (T28D6.9, GI#3873415) open reading frame encodes a 101 amino acid protein. The predicted exon/intron structure of pen-2 has been confirmed by the sequence of an unpublished full-length cDNA (yk569h5 GI# 5572325 and 5558557) present in Genbank. Pen-2 shows a high level of homology with the predicted structures of various human, mouse, rat, and Drosophila proteins, as described in detail below. Pen-2 is a predicted integral membrane protein that, as determined by the structure predicting programs PSORT2 and TopPred2, contains 2 likely transmembrane domains.

Based on several properties, including their own specific phenotypes and their interactions with sel-12, pen-1 and pen-2 likely encode products that interact with presenilins. By extension, other genes with properties in common with pen-1, pen-2, sel-12, or hop-1 can be considered as potential presenilin interacting genes. We have identified the aph-2 gene as a presenilin interacting gene based on 1) the specific phenotypes associated with a loss of aph-2+ function and 2) our identification of novel genetic interactions of aph-2 and with sel-12 and hop-1, and with pen-1 and pen-2.

The aph-2 gene was identified by C. Goutte et al. (1995 International Worm Meeting, abstract 39; 1998 East Coast Worm Meeting, abstract 151; Worm Breeder's Gazette 12(5):27 (1993); Worm Breeder Gazette 13(d):83 (1994)) as a possible component of glp-1 mediated signaling in C. elegans embryos. The aph-2 mutants characterized by these investigators have no reported zygotic phenotypes, but do have maternal embryonic defects, including an Aph phenotype, strikingly similar to glp-1 (ts) embryonic defects. aph-2 reportedly corresponds to the predicted gene ZC434.6. The predicted aph-2 protein is a 721 amino acids in length and is characterized by a signal sequence and 1 to 3 transmembrane domains as predicted by PSORT2 (Nakai K., and Horton P., Trends Biochem Sci, 1999, 24:34–6) and TopPred2 (Claros M G, and von Heijne G. Comput Appl Biosci 1994 December; 10(6):685–6).

The screen that identified pen-1 and pen-2 did not yield mutations in aph-2. In order to identify potential presenilin/aph-2 interactions that may have been missed due to the high stringency of this screen, we investigated a variety of genetic backgrounds that are more highly sensitized for presenilin loss. For these experiments, due to the lack of an available aph-2 mutations, we used RNAi to reduce aph-2+ function in selected backgrounds. Injection of aph-2 dsRNA into the germ line of wild type hermaphrodites results in highly penetrant embryonic lethality among the progeny, with many of the arrested embryos displaying an Aph phenotype. However, injected hermaphrodites still produce a substantial fraction of viable progeny that grow to adulthood with no phenotypic abnormalities in somatic tissues. These worms can be considered "transient escapers" because many of them produce developmentally-arrested Aph embryos. We were thus able to inject adult hermaphrodites with aph-2 RNA and examine their transient escaper progeny for presenilin-dependent phenotypes. Table 4 summarizes the results of these experiments.

TABLE 4

Enhancement of presenilin and pen gene phenotypes by aph-2 RNAi (transgene escaper progeny phenotypes).

| Genotype1 | Zygotic Phenotypes (no aph-2 RNAi) | Zygotic phenotypes after aph-2 RNAi 2 |
|---|---|---|
| wild type | wild-type | wild-type |
| sel-12Δ | Egg-laying defective | Egg-laying defective |
| sel-12Δ; hop-1(ep168)/+ | Egg-laying defective | glp-1 like sterility (12%) |
| hop-1(ep171)3 | Low penetrance glp-1 like sterility (<1%) | glp-1 like sterility (>50%) |
| pen-1(ep140) | Egg-laying defective | glp-1 like sterility (>50%) |
| pen-2(ep220) | Egg-laying defective | glp-1 like sterility (>50% |

1 Complete genotypes of XX hermaphrodites were as follows: Row 1: N2 (wild-type). Row 2: sel-12(ep6). Row 3: sel-12(ep6); hop-1(ep168) unc-74 (x19)/ hT2 [hop-1 + unc-74+]. Row 4: hop-1(ep171) unc-74(x19). Row 5: unc-29(e1072) pen-1(ep140) Row 6: pen-2(ep220) dpy-18(e364).

2 Hermaphrodites from homozygous or heterozygous stocks were injected with aph-2 dsRNA.

All genotypes segregated developmentally-arrested Aph-2 embryos, as well as some viable escaper progeny. For genotypes where aph-2(RNAi) resulted in a zygotic Glp-1- like sterility among the escaper progeny, the approximate fraction of Glp sterile worms is indicated.

Aph-2 RNAi in a homozygous sel-12Δ background does not obviously enhance sel-12 to more severe presenilin phenotypes. However, significant enhancement is detected in homozygous sel-12Δ worms that are also heterozygous for a hop-1 nonsense mutant (hop-1(ep168)/+). With aph-2 RNAi, about 12% of sel-12Δ; hop-1(ep168)/+ animals display glp-1-like sterility, something never seen for this genotype in the absence of aph-2 RNAi. Further, the aph-2 RNAi enhancement is dependent on combined reduction in both presenilins as no interaction is seen with the sel-12Δ.

An additional interaction with aph-2 is observed with an unusual hop-1 allele, ep171. This allele carries a D to N missense alteration in an conserved aspartate residue that corresponds to the Asp385 residue (located in TM domain 8) of human PS1. A PS1 Asp285Ala mutation results in loss of PS1 function, and also has dominant negative effects on PS1+ expression (Wolfe, M. Nature (1999) 398: 513–517) Like the PS1 D385A alteration, hop-1(ep171) has no wild type presenilin activity: the sel-12Δ; hop-1(ep171) double mutant has a glp-1-like sterility defect similar to sel-12Δ; hop-1Δ. In a sel-12+ background, hop-1(ep171) results in a very low penetrance (<1%) glp-1-like sterility phenotype, which suggests it must have dominant negative effects on sel-12 presenilin function or expression. We found that RNAi of aph-2 in homozygous hop-1(ep171) hermaphrodites results in highly penetrant glp-1-like sterility (>50% of viable progeny), indicating a strong additive interaction between reduced aph-2+ function and the hop-1(ep171) dominant effects.

Finally, we also observed that aph-2 RNAi strongly enhances pen-1 and pen-2 mutant phenotypes. Homozygous adult pen-1 and pen-2 hermaphrodites segregating from heterozygous stocks have a normal-appearing germline and never exhibit glp-1-like sterility. In contrast, the corresponding pen-1; aph-2(RNAi) and pen-2; aph-2(RNAi) hermaphrodites display glp-1-like sterility at high penetrance (>50% of viable pen-1 or pen-2 homozygous progeny). These observations demonstrate that a variety genetic backgrounds with partially reduce presenilin pathway activity can be enhanced to stronger phenotypes by an RNAi-mediated reduction in aph-2 activity. The data demonstrate a functional interaction of aph-2 with presenilins and pen-1 and pen-2.

Structure of APH-2 and APH-2 related human and fly proteins. APH-2 contains a PSORT2 predicted cleavable signal sequence and 1 to 3 transmembrane domains predicted by PSORT2 and TopPred2. APH-2 is 18% identical in amino acid sequence to the predicted human protein encoded by the nearly full-length cDNA KIAA0253 (Nagase, T. et al. DNA research (1996) 3: 321–329). In addition, APH-2 shows a similar level of identity to a *Drosophila* protein predicted from contigged ESTs generated at Exelixis, Inc. The human and *Drosophila* APH-2 related proteins are 30% identical and Clustal alignments of the 3 proteins show conservation over entire length of each protein.

Methods: RNA mediated interference (RNAi). RNAi of specific genes was generally done using dsRNA prepared from templates of PCR-amplified genomic DNA fragments. The 5' end of the PCR primers contained the promoter sequences for T7 RNA polymerease and the 3' regions were designed such that they amplified one or more exons of the targeted gene. PCR reactions, employing 5 mmole of each primer, and 0.5 mg of wild-type genomic in a 50 ml reaction, were done using the Expand kit (Roche Biochemicals, Summerville, N.J.), according to the manufacture's protocols. The PCR conditions were as follows: an initial denaturation at 95 C for 30 sec, followed by 35 cycles of 94 C for 30 sec, 55 C for 15 sec, 72 C for 1 min, and a final extension at 72 C for 3 min. Amplified DNA was ethanol precipitated and resuspended in 20 ml of RNAse-free water. A portion of the PCR product was used as template for a T7 polymerase-directed in vitro transcription reaction according to the manufacturer's instructions (Promega, Inc). Reactions were precipitated with ethanol and RNA was resuspended in 20 ml of RNAse-free water and 10 ml 3× IM buffer (20 mM KPO4 pH7.5, 3 mM K+Citrate pH 7.5, 2% PEG 6000). The complementary sense- and anti-sense RNAs were annealed by incubation at 68 C for 10 minutes, followed by incubation 37 C for 30 minutes, and then centrifuged through a 0.45 um cellulose acetate filter. Microinjection of RNA was done as described (Fire et al., Development (1991) 113:503–514) using hermaphrodites at the L4 or young adult stage. Injected worms were recovered in M9 buffer (per liter: 30 g Na2HPO4, 15 g KH2PO4, 2.5 g NaCl, 5 g NH4Cl) for 10–30 minutes, transferred to individual plates, and then transferred to new plates daily. The first generation self-progeny of injected hermaphrodites were inspected for RNAi induced phenotypes by observation in the dissecting microscope or in the compound microscope equipped with Nomarski differential interference optics.

*C. elegans* strains used. Methods for handling and culturing *C. elegans* have been described (Brenner, S. Genetics (1974) 77: 71–94). *C. elegans* variation. Bristol strain N2 represents wild type and is largely isogenic with most of the mutant strains used here. Specific mutations used for genetic mapping and characterization included: LG I-unc-74(×19), dpy-5(e61), unc-29(e1072), fog-3(q443), dpy-24(s71). LG III-dpy-19(e1259ts), unc-119(e2498), pha-1(e2123), dpy-18 (n499 or e364). LG IV-him-8(e1489). LG X lon-2(e678). Rearrangements: mnDp66 (X; I). All are described in *C. elegans* II. Deletion mutations that remove most or part of the of sel-12 or hop-1 coding region are described below. Because the sel-12 gene is sex-linked and sel-12 mutants are mating defective, the transfer of sel-12Δ between strains was usually accomplished using males that carry the chromosomal duplication mnDp66 (X; I) which carries a complementing sel-12+ allele.

SNP Screening by DHPLC: Candidate SNPs were amplified separately from CB4856 and N2 genomic DNA. The PCR products were mixed, denatured and reannealed to create heterozygote molecules for screening by Denaturing HPLC (DHPLC). Each SNP was screened at 5 different temperatures using the same separation gradient. A SNP was deemed authentic when a heteroduplex was detected in the heterozygous state but not in the homozygous starting strains. The appropriate temperature for each SNP was noted and used for screening that SNP on recombinant worms.

SNP Scoring on recombinant worms: Lysates from appropriate recombinants were used as genomic DNA templates for amplifying the SNPs by PCR. These crude PCR products were then run on DHPLC using the appropriate temperatures for each SNP identified above. For each recombinant, each SNP was typed and the data input into a spreadsheet at random. The physical order of the SNPs was then determined from AceDB. This generated a haplotype for each recombinant, and the locations at which recombination events occurred was noted.

Isolation and characterization of sel-12 and hop-1 deletion mutant strains. Deletion alleles of sel-12 and hop-1 were obtained by the two-step method of Plasterk (Plasterk, R. C.

*elegans*: Modern Biological Analysis of an Organism (1995) pp. 59–80) using mut-2 as a source of Tc1 transposon mutator activity. sel-12(ep6) (hereinafter referred to as sel-12Δ) is a deletion mutation that removes amino acids 34 to 441 of the sel-12 open reading frame. hop-1(ep90) (hereinafter referred to as hop-1) is a 722 bp deletion that starts at amino acid 216 in the hop-1 open reading frame and terminates within the gene's 3' untranslated region. The sel-12Δ and hop-1Δ single mutants were backcrossed at least 10 times to wild-type (*C. elegans* variation. bristol strain N2, supra) before phenotypic characterization and construction of double mutants. The sel-12Δ single mutant has an egg-laying defective phenotype similar to that of previously-described sel-12(1 f) mutants (Levitan, D. and Greenwald, I. Nature (1995) 377:351–354). The hop-1Δ mutant has no gross phenotypic abnormalities, similarly to hop-1 deletion alleles described by others (Westlund, B. et al. Proc. Natl. Acad. Sci (1999) 96: 2497–2502).

To provide a source of sel-12Δ; hop-1Δ double mutants that lack maternal sel-12+ activity, we constructed a balanced sel-12Δ/sel-12Δ; hop-1Δ +/+ unc-74 strain. This strain segregates doubly mutant sel-12Δ; hop-1Δ hermaphrodites that exhibit a completely penetrant sterile phenotype with germline proliferation defects characteristic of glp-1(1f) mutants (Austin, J. and Kimble, J., Cell (1987) 51:589–599). In addition, these worms have a fully penetrant 2 anchor cell phenotype and an everted vulva phenotype that is reminiscent of vulval defects caused by lin-12(1f) mutations.

Isolation of enhancers of sel-12Δ. Enhancer alleles of pen-1 and pen-2 were obtained after mutagenesis of a homozygous sel-12Δ strain or, in later experiments, a sel-12Δ; unc-74(×19) strain (the unc-74 mutation lies near hop-1 on chromosome I and was included to provide a built-in mapping resource). XX hermaphrodites of either genotype were mutagenized with ethyl methane sulfonate as described (Brenner, S. Genetics (1974) 77: 71–94). In the F1 generation, one (or sometimes two) hermaphrodites were picked onto individual growth plates (approximately 55,000 plates total). Three to five days later, the plates were screened for the appearance of sterile F2 progeny with a "dark" appearance indicative of a defect in germline proliferation. Candidate sterile mutants were then screened by Nomarski difference interference microscopy to identify those which exhibit glp-1 like sterility similar to sel-12Δ; hop-1Δ worms.

A set of 44 candidates identified in this way were subjected to a cross scheme designed to determine whether or not the sterile phenotype in these mutants was dependent on the worm's sel-12 genotype as would be expected for a sel-12 enhancer. For this test, each candidate was crossed to dpy-19 III; him-8; lon-2 males and the resulting cross-progeny were picked onto individual plates. In the following generation, the presence of sterile lon-2/lon-2 progeny (which are sel-12+/sel-12+ in the absence of recombination) indicate that sterile phenotype was not dependent on a loss of sel-12+ activity and was possibly due to a mutation in one of the known glp-1 pathway genes (glp-1, lag-1, lag-2). 29 candidates analyzed in this way were sel-12 independent and thus were rejected as possible presenilin enhancers. For 26 of the 29 rejected candidates, the mutation causing sterility segregated in trans to dpy-19, which is the expected behavior for a glp-1 allele. 9 of these LG III mutations failed to complement the sterile phenotype of known glp-1 alleles; the other 17 LG III mutations were not tested.

For the remaining 15 candidates, the Glp sterile phenotype did not reappear in the F2 generation, a result consistent with the presence of an enhancer mutation whose interaction with sel-12 is rescued by maternal sel-12+ activity. This explanation was tested by picking sel-12/sel-12 worms in the F2 generation onto individual plates and examining their progeny for reappearance of glp-1-like sterility in the next generation. This was the result observed for each of the remaining 15 candidates. A combination of complementation tests, meiotic mapping, and sequence analysis of mutant alleles demonstrated that the each candidates carried a mutation in either hop-1 (8 candidates) or in either of two newly-identified genes, pen-1 (4 candidates) or pen-2 (3 candidates).

Pen-1 mapping, characterization, cloning, and computational analysis: Genetic mapping of pen-1 was done in sel-12Δ backgrounds and was based on the glp-1-like sterility phenotype of doubly mutant pen-1; sel-12Δ worms. We initially mapped pen-1(ep140) to chromosome I between unc-29 and dpy-24. Further mapping with visible markers narrowed the position to between unc-29 and fog-3, a 1.1 MB interval. From heterozygotes of the genotype pen-1/unc-29 fog-3 trans-heterozygotes, $^{16}/_{20}$ Unc-29 non-Fog-3 recombinants and ¼ Fog-3 non-Unc-29 recombinants segregated pen-1.

Finer mapping was done using SNP markers that are polymorphic between the N2 Bristol strain from which pen-1 mutants were derived and strain CB4856 Hawaiian strain of *C elegans*. The Genome Sequencing Center (St. Louis, Mo.) has identified an large number of potential SNPs in CB4856 (http: //genome.wustl.edu /gsc/ CEpolymorph /snp.shtml). Four of these potential SNPs in the unc-29 to fog-3 interval were confirmed by testing with an SNP genotyping assay that is based on separation of heteroduplex PCR products by denaturing HPLC (Underhill Pa., et al., Genome Res. 1997 October;7(10):996–1005). Initial mapping against these SNPs was done by constructing heterozygotes of the genotypes unc-29 pen-1/CB4856 or pen-1 dpy-24/CB4956 and picking Unc-29 non-Pen-1 or Dpy-24 non-Pen-1 recombinants. Additional non-Pen-1 recombinants were isolated from unc-29 pen-1 fog-3/CB4856 heterozygotes. Among 50 Unc-29 non-Pen-1 recombinants, 9 had cross-overs occurring to the right of the C31H5 SNP, placing pen-1 to the right of this marker. Among a combined set of 45 Dpy-24 non-Pen-1 or Fog-3 non-Pen-1 recombinants, 4 had cross-overs to the left of the F14B4 SNP, placing pen-1 left of this marker. The combined data positioned pen-1 to the ~240 KB interval between the C31H5 and F14B4 SNPs.

For mapping pen-1 to smaller intervals, additional SNPs lying in the C45G3 to F14B4 interval were identified by DNA sequencing. Six approximately 2 KB segments of DNA in the interval were amplified by PCR of N2 and CB4856 genomic DNA and end sequenced. In some cases, additional sequencing primers were used to generate internal sequence. SNPs between N2 and CB4856 were identified by sequence alignment and ~200 bp PCR products were designed around each high quality candidate. These 200 bp products were screened and scored by DHPLC as described above. This analysis positioned pen-1 between 2 SNPs, one on cosmid C45G3 and the other on cosmid F36H2, that lie approximately 52 KB from one another.

Mutation detection. Two single nucleotide polymorphisms (SNPs), labeled C45G3A and F36H2A, defined a 52 kb genomic interval, pen-1, within which seven predicted candidate genes resided. A 30 kb gene-rich section of this 52 kb interval was resequenced in 3 worms whose mutation had been mapped genetically to this region, ep140, ep169, and ep170. All DNA sequencing reactions were performed using standard protocols for the BigDye sequencing reagents (Applied Biosystems, Inc. Foster City, Calif.) and products were analyzed using ABI 377 DNA sequencers.

Trace data obtained from the ABI 377 DNA sequencers was analyzed and assembled into contigs using the Phred-Phrap programs (Gordon, Genome Res. (1998) 8:195–202). The resequence data was then compared to the wildtype strain, N2, for polymorphism. This analysis identified a third position base change, G to an A, at 191AA in the VF36H2L.1 gene (GI# 2815036) in three pen-1 alleles, ep140, ep169 and ep170, resulting in an amino acid change from a tryptophan (W) to stop (*). Further sequencing analysis of unmapped mutants revealed another mutation in worm ep216 within the same codon, but in the second position, also a G to an A, resulting in the same amino acid change. Analysis of human pen-1 led us to identify the novel pen-1B protein.

Pen-2 mapping, characterization, cloning, and computational analysis. We initially positioned pen-2(ep220) to the left of unc-25 on chromosome III. From hermaphrodites of the genotype pen-2/dpy-18 unc-25, 4/4 non-Dpy-18 Unc-25 recombinants segregated pen-2 and 0/21 Dpy-18 non-Unc-25 recombinants segregated pen-2. Of 70 dpy-18 unc-25 homozygotes picked from the same heterozygous hermaphrodites, only 2 segregated pen-2, indicating that pen-2 lies relatively close to dpy-18 and probably to the left of this gene. Further mapping positioned pen-1 between pha-1 and dpy-18: from pen-1/pha-1 dpy-19; sel-12Δ hermaphrodites, 1/14 non-Pha-1 Dpy-1 recombinants picked up pen-2. These data positioned pen-2 between pha-1 and dpy-18 interval, an approximately 240 KB interval, and suggested pen-2 lies close to dpy-18.

Identification of pen-2 as predicted gene T28D6.9: We determined that pen-2 is the predicted gene T28D6.9 (GI#3873415) based on 1) RNAi of predicted genes in the pha-1 to dpy-18 interval and 2) mutation detection. For 28 of the 31 genes in the interval, primers tailed with T7 promoter sequence were used to amplify selected coding region using either a first-strand cDNA pool or genomic DNA as template as described above. Double-stranded RNA was synthesized from each PCR product and injected into sel-12Δ homozygotes. RNAi of T28D6.9 produced the expected pen-2 phenotypes among the progeny of injected worms, including glp-1-like sterility in sel-12Δ worms and an Aph embryonic arrest phenotype after injection into N2 and sel-12Δ worms. Mutation detection of the T28D6.9 open reading frame identified nonsense mutations in each of three pen-2 alleles (ep219, ep220, ep221). Briefly, The single mutant in this group, ep220, was tested by sequencing a PCR product amplified in an ep220 lysate and wild-type strain. This analysis identified a G to A mutation at 74AA that resulted in a tryptophan (W) to stop (*). Additional sequencing analysis of unmapped mutants revealed that there were 2 more mutants in this group. The ep219 worm had a G to A change in the third position of 74AA that produced a W to a *. The ep221 worm had a G to A change in another W that also resulted in a stop codon at 36AA. These three changes all effect highly conserved trytophans that could significantly alter or ablate the function of the T28D6.9 gene.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for specifically detecting a stress that alters a functional interaction of a presenilin enhancer (pen) polypeptide with Notch processing or with amyloid precursor protein (APP) processing in a *C. elegans* cell in situ which provides a functional interaction of a pen polypeptide with Notch or APP processing, wherein the stress is a modulator of Notch or APP processing, wherein the pen polypeptide comprises a wild-type pen selected from the group consisting of *C. elegans* (SEQ ID NO:7) Pen-2 and *C. elegans* (SEQ ID NO:1) Pen-1, wherein said cell is stressed by a disruption of a pen gene function, said disruption sufficient to provide a sensitized Notch or APP processing pathway, the method comprising steps:
   a) subjecting said cell to a putative modulator of Notch or APP processing; and
   b) detecting a resultant change in Notch or APP processing in the cell, wherein said change identifies the putative modulator as a modulator of Notch or APP processing, and thereby detecting said stress,
   wherein the disrupting is effected by (i) genomic disruption of the pen gene, (ii) RNAi-mediated interference with expression of the pen gene, or (iii) antisense RNA interference with expression of the pen gene, and wherein the disrupting provides non-natural or pathogenic expression of the pen gene.

2. The method according to claim 1, wherein the putative modulator is a chemical agent.

3. The method according to claim 1, wherein the putative modulator is an organic compound from a small molecule library.

4. The method according to claim 1, wherein the putative modulator is an RNAi.

5. The method according to claim 1, wherein the putative modulator is an aph-2 RNAi.

6. The method according to claim 1, wherein the putative modulator is an antibody.

7. The method according to claim 1, wherein the putative modulator is a genetic mutation.

8. The method according to claim 1, wherein the putative modulator is a genetic mutation, and the detecting step comprises detecting a phenotypic change in the organism.

9. The method according to claim 1, wherein the detecting step detects a transcriptional reporter of Notch.

10. The method according to claim 1, wherein the detecting step detects a structural alteration in the pen.

11. The method according to claim 1, wherein the detecting step detects the generation of amyloid-β (Aβ).

12. The method according to claim 1, wherein the detecting step detects the generation of Aβ using an Aβ-specific antibody.

13. The method according to claim 1, wherein the disrupting is effected by genomic disruption of the pen gene.

14. The method according to claim 1, wherein the Notch or APP processing is APP processing.

15. A method for specifically detecting a stress that alters a functional interaction of a presenilin enhancer (pen) polypeptide with amyloid precursor protein (APP) processing, in a *C. elegans* cell in situ, wherein the stress is a modulator of APP processing, wherein said cell is stressed by disrupting a pen gene function, said cell providing a functional interaction of a pen polypeptide with APP processing, said disruption sufficient to provide a sensitized APP processing pathway, wherein the pen polypeptide comprises a wild-type pen selected from the group consisting of *C. elegans* (SEQ ID NO:7) Pen-2, *C. elegans* (SEQ ID NO:1) Pen-1, and *C. elegans* (SEQ ID NO:13) Aph-2, the method comprising steps:
   a) subjecting the cell to a putative modulator of APP processing; and
   b) detecting a resultant change in APP processing in the cell to identify a modulator of APP processing, and thereby detecting said stress,
   wherein the disrupting is effected by (i) genomic disruption of the pen gene, (ii) RNAi-mediated interference with expression of the pen gene, or (iii) antisense RNA interference with expression of the pen gene, and wherein the disrupting provides non-natural or pathogenic expression of the pen gene.

16. The method according to claim 15, wherein the putative modulator is a chemical agent.

17. The method according to claim 15, wherein the putative modulator is an organic compound from a small molecule library.

18. The method according to claim 15, wherein the putative modulator is an RNAi.

19. The method according to claim 15, wherein the putative modulator is an aph-2 RNAi.

20. The method according to claim 15, wherein the putative modulator is an antibody.

21. The method according to claim 15, wherein the putative modulator is a genetic mutation.

22. The method according to claim 15, wherein the putative modulator is a genetic mutation, and the detecting step comprises detecting a phenotypic change in the organism.

23. The method according to claim 15, wherein the detecting step detects a transcriptional reporter of Notch.

24. The method according to claim 15, wherein the detecting step detects a structural alteration in the pen.

25. The method according to claim 15, wherein the detecting step detects the generation of amyloid-β (Aβ).

26. The method according to claim 15, wherein the detecting step detects the generation of Aβ using an Aβ-specific antibody.

27. The method according to claim 15, wherein the disrupting is effected by genomic disruption of the pen gene.

28. A method for specifically detecting a stress that alters a functional interaction of a presenilin enhancer (pen) polypeptide with Notch processing or with amyloid precursor protein (APP) processing in a *C. elegans* cell in situ which provides a functional interaction of a pen polypeptide with Notch or APP processing, wherein the stress is a modulator of Notch or APP processing, wherein the pen polypeptide comprises a wild-type pen selected from the group consisting of *C. elegans* (SEQ ID NO:7) Pen-2 and *C. elegans* (SEQ ID NO:1) Pen-1, wherein said cell is stressed by a disruption of a pen gene function, said disruption sufficient to provide a sensitized Notch or APP processing pathway, the method comprising steps:
   a) subjecting said cell to a putative modulator of Notch or APP processing; and
   b) detecting a resultant change in Notch or APP processing in the cell, wherein said change identifies the putative modulator as a modulator of Notch or APP processing, and thereby detecting said stress,
   wherein the putative modulator is an aph-2 RNAi, the detecting step comprises detecting a phenotypic change in the organism, and the disrupting is effected by genomic disuption of the pen gene.

* * * * *